US009176107B2

United States Patent
Jeffrey et al.

(10) Patent No.: US 9,176,107 B2
(45) Date of Patent: Nov. 3, 2015

(54) SYSTEM AND METHOD FOR MONITORING ASSET HEALTH BY DISSOLVED GAS MEASUREMENT

(71) Applicant: LumaSense Technologies Holdings, Inc., Santa Clara, CA (US)

(72) Inventors: John Paul Jeffrey, Santa Clara, CA (US); Anastasia Rude, Santa Clara, CA (US); Brett Sargent, Santa Clara, CA (US); Eric Wertz, Santa Clara, CA (US); Jeffrey Headrick, Santa Clara, CA (US); Terry M. Stapleton, Santa Clara, CA (US); Prabhu Soundarrajan, Dublin, CA (US)

(73) Assignee: LumaSense Technologies Holdings, Inc., Santa Clara, CA (US)

( * ) Notice: Subject to any disclaimer, the term of this patent is extended or adjusted under 35 U.S.C. 154(b) by 0 days.

(21) Appl. No.: 14/001,947

(22) PCT Filed: Feb. 1, 2013

(86) PCT No.: PCT/US2013/024529
§ 371 (c)(1),
(2) Date: Aug. 28, 2013

(87) PCT Pub. No.: WO2013/116799
PCT Pub. Date: Aug. 8, 2013

(65) Prior Publication Data
US 2014/0053626 A1   Feb. 27, 2014

Related U.S. Application Data

(60) Provisional application No. 61/593,802, filed on Feb. 1, 2012.

(51) Int. Cl.
*G01N 33/18* (2006.01)
*G01N 33/28* (2006.01)
*G01N 1/20* (2006.01)

(52) U.S. Cl.
CPC .......... *G01N 33/2841* (2013.01); *G01N 1/2035* (2013.01)

(58) Field of Classification Search
CPC .............................. G01N 33/28; G01N 33/18
USPC .............. 73/19.1, 23.21, 31.05, 31.07, 19.01, 73/19.02, 19.05; 95/45, 46, 241, 247, 266; 96/6, 174, 193, 155, 182; 210/664, 210/718, 750, 96.2
See application file for complete search history.

(56) References Cited

U.S. PATENT DOCUMENTS 4,664,808 A * 5/1987 Kim .............................. 210/638
5,100,555 A * 3/1992 Matson ............................ 95/44
(Continued)

FOREIGN PATENT DOCUMENTS

DE      19833601 C1    12/1999
WO    03/048719 A2     6/2003

OTHER PUBLICATIONS

International Search Report issued in corresponding International Application No. PCT/US2013/024529; Mailed May 15, 2013 (2 pages).

(Continued)

*Primary Examiner* — Hezron E Williams
*Assistant Examiner* — Hoang Nguyen
(74) *Attorney, Agent, or Firm* — Osha Liang LLP

(57) ABSTRACT

A method for analyzing gas dissolved within a fluid filled asset includes extracting the fluid from the fluid filled asset, circulating the fluid though a first fluid loop, and passing the extracted fluid along a first side of a gas permeable membrane. Gas is extracted from a second side of the gas permeable membrane and the extracted gas is circulated through a second fluid loop. The first fluid loop and the second fluid loop are separated by the gas permeable membrane. The method further includes controlling a pressure differential across the gas permeable membrane to a predetermined pressure differential and providing the extracted gas to a gas analysis unit located within the second fluid loop. The chemical makeup of the extracted gas is periodically determined using the gas analysis unit.

20 Claims, 23 Drawing Sheets

(56) References Cited

U.S. PATENT DOCUMENTS

| | | | |
|---|---|---|---|
| 5,639,375 A * | 6/1997 | Hiroshi | 210/640 |
| 5,749,942 A * | 5/1998 | Mattis et al. | 95/46 |
| 5,876,604 A * | 3/1999 | Nemser et al. | 210/634 |
| 6,037,592 A * | 3/2000 | Sunshine et al. | 250/343 |
| 6,526,805 B1 * | 3/2003 | Babes-Dornea et al. | 73/19.12 |
| 6,716,352 B1 * | 4/2004 | Livingston | 210/634 |
| 7,028,562 B2 | 4/2006 | LaCourse et al. | |
| 7,434,446 B2 | 10/2008 | Johnson et al. | |
| 8,075,675 B2 * | 12/2011 | Mahoney et al. | 96/6 |
| 8,616,045 B2 * | 12/2013 | Cavallini et al. | 73/19.11 |
| 2005/0086998 A1 | 4/2005 | Qin | |
| 2007/0256969 A1 | 11/2007 | Ding et al. | |
| 2009/0255900 A1 * | 10/2009 | Qin | 216/64 |
| 2010/0077828 A1 | 4/2010 | Herz et al. | |
| 2011/0303590 A1 * | 12/2011 | Childers et al. | 210/96.2 |

OTHER PUBLICATIONS

Written Opinion issued in corresponding International Application No. PCT/US2013/024529; Mailed May 15, 2013 (4 pages).

Duval, M., "A Review of Faults Detectable by Gas-in-Oil Analysis in Transformers", IEEE Electrical Insulation Magazine, vol. 18, No. 3, pp. 8-17, Jun. 30, 2002 (10 pages).

Duval, M., "New techniques for dissolved gas-in-oil analysis", IEEE Electrical Insulation Magazine, vol. 19, No. 9, pp. 6-15, Apr. 30, 2003 (10 pages).

International Preliminary Report on Patentability issued in corresponding International Application No. PCT/US2013/024529 dated Aug. 14, 2014 (6 pages).

Search Report issued in corresponding European Application No. EP13742890; Dated Aug. 10, 2015 (6 pages).

* cited by examiner

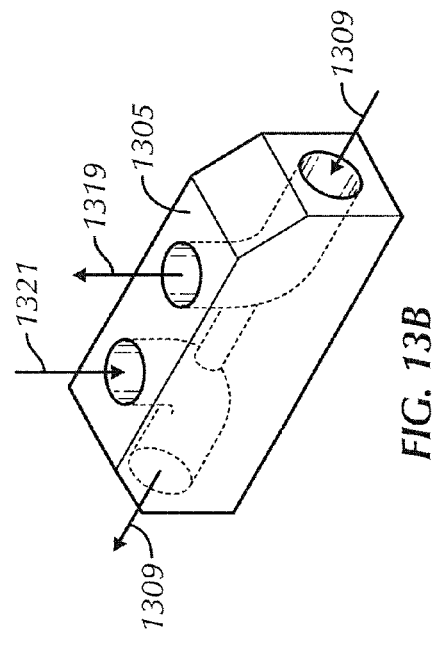
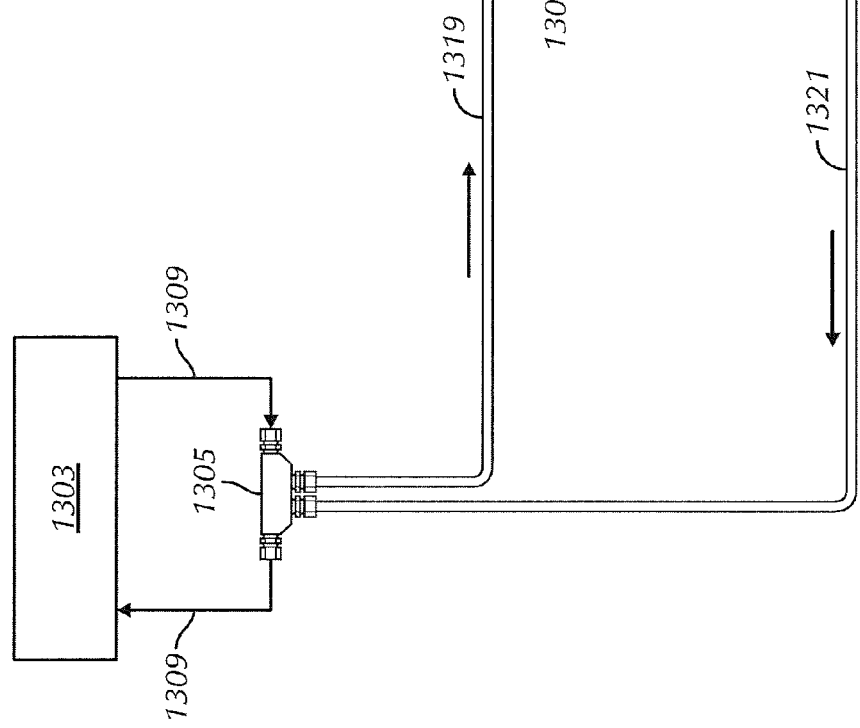

| Monitor Response (gas in oil) | LTC condition Probable cause and fix | User Action / Recommenation for Lab DGA analysis* |
|---|---|---|
| No rapid rise of ethylene and acetylene Ethylene / Acetylene<1 | Normal | Sample every six months |
| Rapid rate of rise of acetylene above 1000ppm | Caution Mechanical activity in LTC | Put LTC in watch list, sample every three months |
| Ethylene Rise (1000 to 5000ppm) AND Ethylene rise > Acetylene rise Ethylene / Acetylene > 1 | Warning ("amber") Point at which problem is detectable by eye Enter and repair now point | LTC approaching "critical condition" sample within 1 mo. Replace LTC after confirming with lab analysis in 1-2 weeks |
| Massive rate of rise of C2H4 Ethylene / Acetylene >>1 | Alarm Enter and repair now point Major damage to LTC requiring complete overhaul | LTC is "extremely critical condition" Need attention in 1 day and take LTC offline |

*Note: The user action / recommendations are not part of the instrument

FIG. 18

SYSTEM AND METHOD FOR MONITORING ASSET HEALTH BY DISSOLVED GAS MEASUREMENT

BACKGROUND

It is widely accepted that a cost effective, dedicated online gas monitoring can provide early diagnostics for transformer failures and enable utilities to a move to condition based asset management programs. Current online DGA technologies are often cost-prohibitive to address a wide fleet of load tap changers ("LTCs") and transformers. As a result, unexpected failures due to LTC condition and transformer faults still occur that result in expensive outages and power delivery interruption. Accordingly, the demand for real-time, low-cost online DGA monitors is increasing for the aging utility infrastructure.

Fault conditions in power transformers and LTCs cause the breakdown of the insulating oil and paper inside the power transformer or LTC. The breakdown creates gases in the insulating oil. The dissolved gases in the oil are indicative of the fault. So the goal is to measure the dissolved gases in the oil and use their levels to indicate the health of the power transformer or LTC. In order to measure the dissolved gases in the oil of a power transformer or LTC, the gases must be separated from the oil.

SUMMARY

In general, in one aspect, one or more embodiments are directed to a method for analyzing gas dissolved within a fluid filled asset. The method includes extracting the fluid from the fluid filled asset, circulating the fluid though a first fluid loop, and passing the extracted fluid along a first side of at least one gas permeable membrane. The method further includes extracting gas from a second side of the at least one gas permeable membrane, circulating the extracted gas through a second fluid loop, wherein the first fluid loop and the second fluid loop are separated by the at least one gas permeable membrane. The method further includes controlling a pressure differential across the at least one gas permeable membrane to a predetermined pressure differential and providing the extracted gas to a gas analysis unit disposed within the second fluid loop. The chemical makeup of the extracted gas is periodically determined using the gas analysis unit.

In another aspect, one or more embodiments are directed to a system for analyzing dissolved gas in a fluid filled asset. The system comprises a fluid extraction unit configured to extract fluid from the fluid filled asset, a fluid pump configured to circulate the fluid though a first fluid loop, a gas extraction unit in the first fluid loop configured to extract dissolved gas from the circulating fluid. The gas extraction unit includes at least one gas permeable membrane. The system further includes a gas pump configured to circulate the extracted gas through a second fluid loop, wherein the first fluid loop and the second fluid loop are separated by the at least one gas permeable membrane. A pressure control unit is configured to control the differential pressure across the at least one gas permeable membrane to a predetermined pressure differential. A gas analysis unit is included in the second fluid loop, and is configured to receive the extracted gas, wherein the gas analysis unit is further configured to periodically determine, at specific intervals, the chemical makeup of the extracted gas.

Other aspects of the embodiments disclosed herein will be apparent from the following description and the appended claims.

BRIEF DESCRIPTION OF DRAWINGS

FIG. 13A shows a block diagram of a flow through installation of a system for monitoring asset health by dissolved gas measurement in accordance with one or more embodiments.

FIG. 13B shows an adaptor for a flow through installation in accordance with one or more embodiments.

FIG. 18 shows one example methodology used in the instrument in accordance with one or more embodiments.

DETAILED DESCRIPTION

Figure 1:
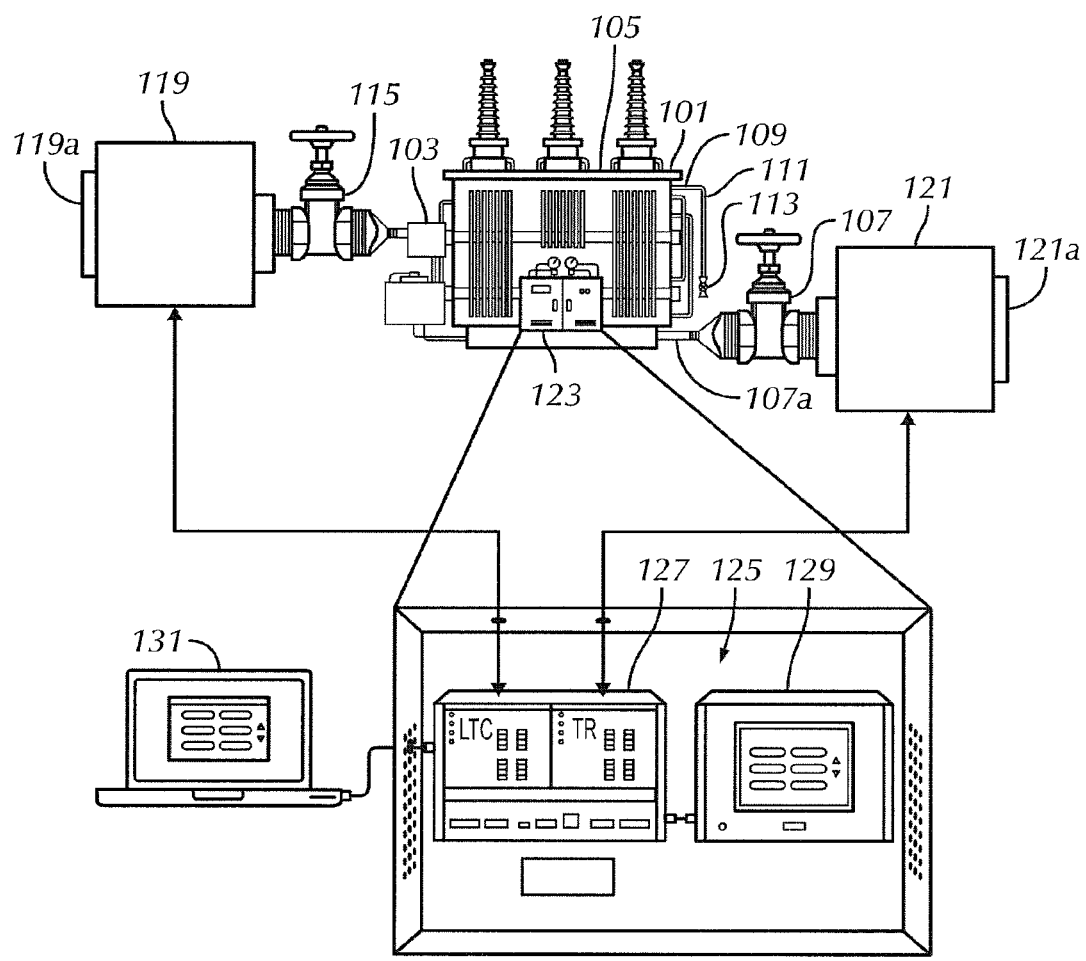
FIG. 1 shows a system for monitoring asset health by dissolved gas measurement in accordance with one or more embodiments.

Specific embodiments will now be described in detail with reference to the accompanying figures. Like elements in the various figures are denoted by like reference numerals for consistency.

In the following detailed description of embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, one or more embodiments are directed to a system and method for cost-effectively monitoring the health of oil filled electrical equipment, also more generally referred to herein as an oil filled asset, i.e., any oil filled piece of equipment that may be monitored for the presence of dissolved gases within the oil. More specifically, the system and methods disclosed herein are directed to monitoring the chemical makeup and quantity of gases that are dissolved within the oil contained within the oil filled asset, e.g., dielectric oil within transformers and/or load tap changers. As used herein, the term fluid or oil filled asset encompasses partially or fully filled assets. Furthermore, as used herein the term fluid is used generally to refer to both liquids and gases, e.g., oil and the gases separated from the oil.

FIG. 1 shows an example of an oil filled asset to be monitored in accordance with one or more embodiments. Specifically, FIG. 1 shows an oil filled transformer 101 that includes a load tap changer ("LTC") 103. In addition, located near the bottom of the transformer main tank 105 is a transformer oil drain pipe 107a and oil drain valve 107. Furthermore, near the top of transformer main tank 105 is an oil fill inlet 109. The transformer shown in FIG. 1 is further equipped with an oil fill line 111 that connects to oil fill inlet 109 and extends downward toward oil drain valve 107. Attached to the end of oil fill line 111 is oil fill valve 113. In accordance with one or more embodiments, the system for monitoring asset health by dissolved gas measurement may be attached to the LTC 103 or transformer main tank 105 by way of any one of a number of adaptors as described in more detail below in reference to FIGS. 6-13.

Figure 9:
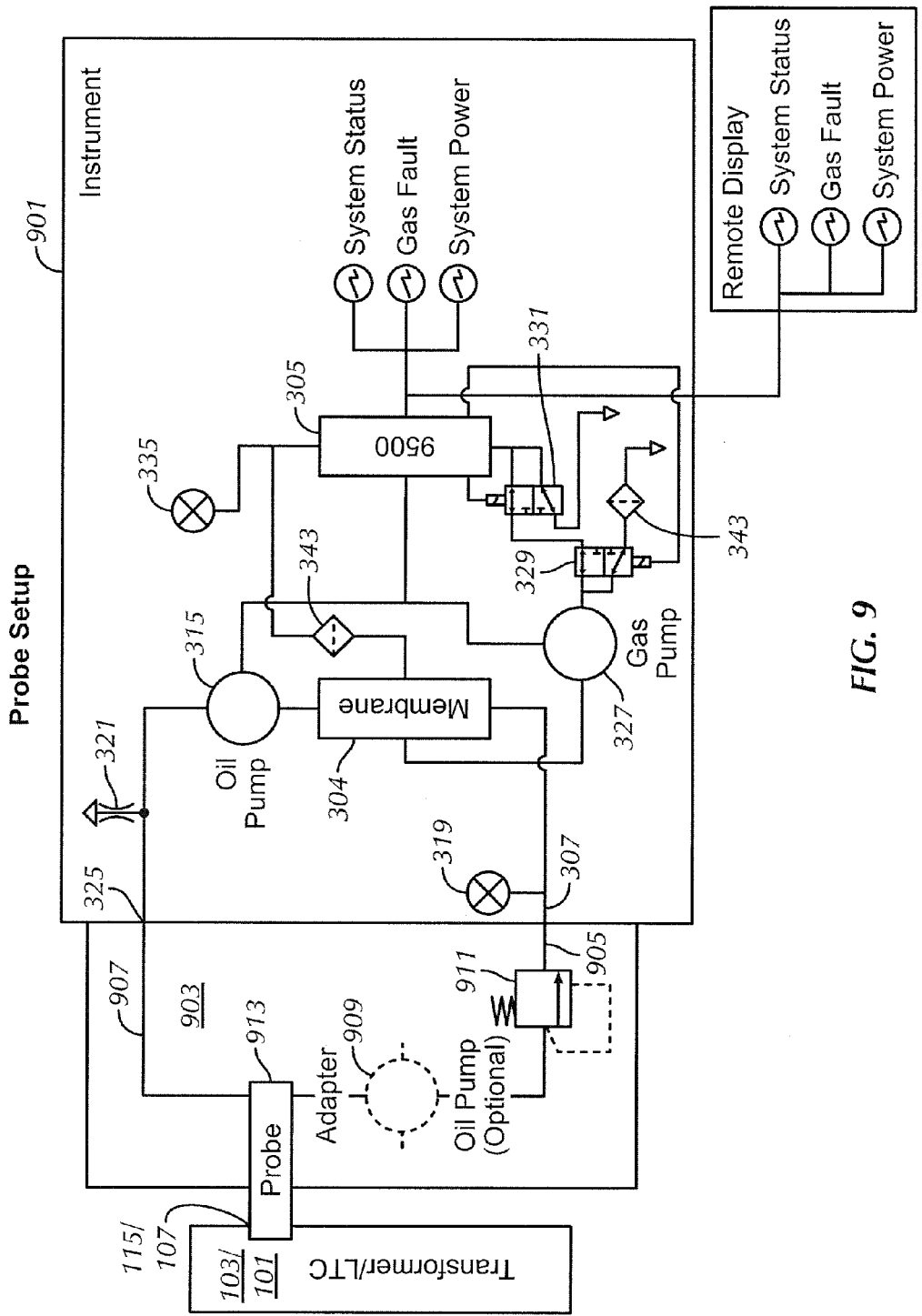
FIG. 9 shows a block diagram of a single valve installation of a system for monitoring asset health by dissolved gas measurement in accordance with one or more embodiments.
Figure 10:
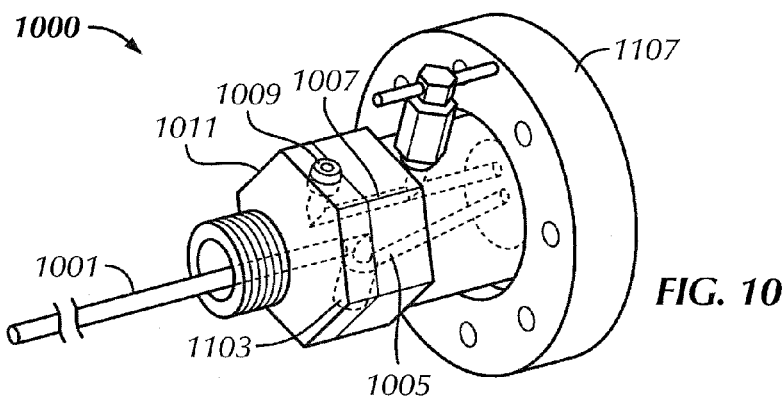
FIG. 10 shows an example of an adaptor for a single valve installation in accordance with one or more embodiments.

In accordance with one or more embodiments, the oil filled LTC 103 may be monitored using the system for monitoring asset health by dissolved gas measurement. According to this embodiment, a monitor module 119 may be attached to the LTC 103 by way of a single LTC valve 115. In this single valve configuration, the monitor module 119 may be attached by way of an adaptor as described below in reference to FIGS. 9-11. In another embodiment, the monitor module 119 may be connected directly into the oil filtration loop of the LTC as described below in reference to FIGS. 12-13. In another embodiment, for where main tank 105 of the oil filled transformer 101 is to be monitored, either separately or concurrently with the LTC 103, a monitor module 121 may be attached by way of oil drain valve 107. In this single valve configuration, the monitor module 121 may be attached by way of an adaptor as shown in FIG. 9-11. According to yet another embodiment, the monitor module 121 may be attached in a two-valve configuration i.e., connected to both oil drain valve 107 and oil fill valve 113. In this two valve configuration, the monitor module 121 may be attached by way of an adaptor, as described below in reference to FIGS. 7-8.

In accordance with one or more embodiments, in a single valve installation, the adaptor may include a probe that is configured in an internal dual-passage geometry that includes an oil inlet passage through which oil from the asset is extracted and an oil outlet passage through which fluid is returned to the asset; oil is extracted and returned through a single valve, e.g., the LTC valve 115 or the oil drain valve 107. In other examples, the adaptor may have passages for receiving two lines, e.g., so as to connect to both the oil drain valve 107 and the oil fill valve 113 and/or to connect to a flow line used in the LTC filter loop, making use of existing pumps and plumbing for circulation of the oil through the oil circulation loop of the analysis unit. Alternatively, oil may be drawn from the filtration loop in order to feed the oil circulation loop of the analysis unit which itself may employ at least one oil pump for oil circulation. One of ordinary skill having the benefit of this disclosure will appreciate that the standard LTC filtration subsystem includes various pumps, filters, valves, etc. For simplicity these components will not be described in detail here. As used herein, the above-described configuration is referred to as the flow-through configuration and is shown in more detail in FIGS. 12-13.

Advantageously, systems employing the two-valve, probe, or flow-through configurations may be configured by the proper choice of adaptor, based on the nature of the particular installation and thus are highly tailored to end user needs. Accordingly, the monitor module itself need not be redesigned for each installation. Thus, in each of the above installation scenarios, the same system may be installed using different adaptors, allowing for great flexibility and reduced cost.

Also shown in FIG. 1 is an analysis unit 125 that is conveniently mounted on the surface of the transformer main tank for easy visibility and easy access, e.g., within the transformer control cabinet 123. In accordance with one or more embodiments, the analysis unit 125 includes a drive hub 127 and a controller 129 that are both operably connected to one or more monitor modules, e.g., monitor modules 119, 121, or the like. In accordance with one or more embodiments, a monitor module may include the necessary plumbing for connecting the monitor to the oil filled asset, e.g., transformer or LTC, as described in more detail below in reference to FIGS. 3-5. In accordance with one or more embodiments, a monitor module also includes the necessary pumps, valves, sensors, heater, etc., for extracting oil from the oil filled asset, controlling the pressure and temperature of the oil within an oil circulation loop. In addition, each monitor module may be controlled and/or powered by drive hub 127. A monitor module also includes a respective indicator light, e.g., indicator lights 119a and 121a for easily determining the state (or health) of the transformer. For example, the indicator light may vary from green to yellow to blue to red to indicate normal, caution, warning, or alarm, respectively. In accordance with one or more embodiments, drive hub 127 is a versatile hub that includes the necessary relays, control/communication electronics, and power supply for a number of instruments and may be field programmable and upgradable. For example the drive hub 127 may be a LumaSense EZHUB device.

In accordance with one or more embodiments, the controller 129 may provide for gas readings that are viewable by a user and may drive, display data from, communicate with up to 32 instruments at a time. For example, the controller 129 may provide advanced communications, local display, and memory to enhance Smart Grid integration and performance. Furthermore, the controller 129 may provide for an interactive touch screen display for set-up, alarms, notifications and analysis of dissolved gas data received from the analysis units. Furthermore, the controller 129 may employ communication protocols such as Modbus ASCII, Modbus RTU, DNP3.0, ASCII, IEC61850, or traditional RS485, RS232, and Ethernet communications. In accordance with one or more embodiments, the controller 129 may interact with a number of drive hubs 127 via RS485, Ethernet connection, or any other communication protocol. Furthermore, the controller 129 may include volatile and nonvolatile memory for data storage that may be used, e.g., to log and store dissolved gas data over the lifetime of a transformer, i.e., (40 years).

As shown in FIG. 1, in accordance with one or more embodiments, the drive hub 127 and/or the controller 129 may be accessed and/or controlled by way of a remote computing device such as a remote mobile device 131, e.g., a laptop, mobile phone, smart phone, tablet pc, or the like. One of ordinary skill will appreciate that the remote mobile device may be access by wire or wireless, LAN WAN (including the broader internet), WIFI, Bluetooth, ZiGBee, or the like and is not limited to wired communication.

Figure 2:
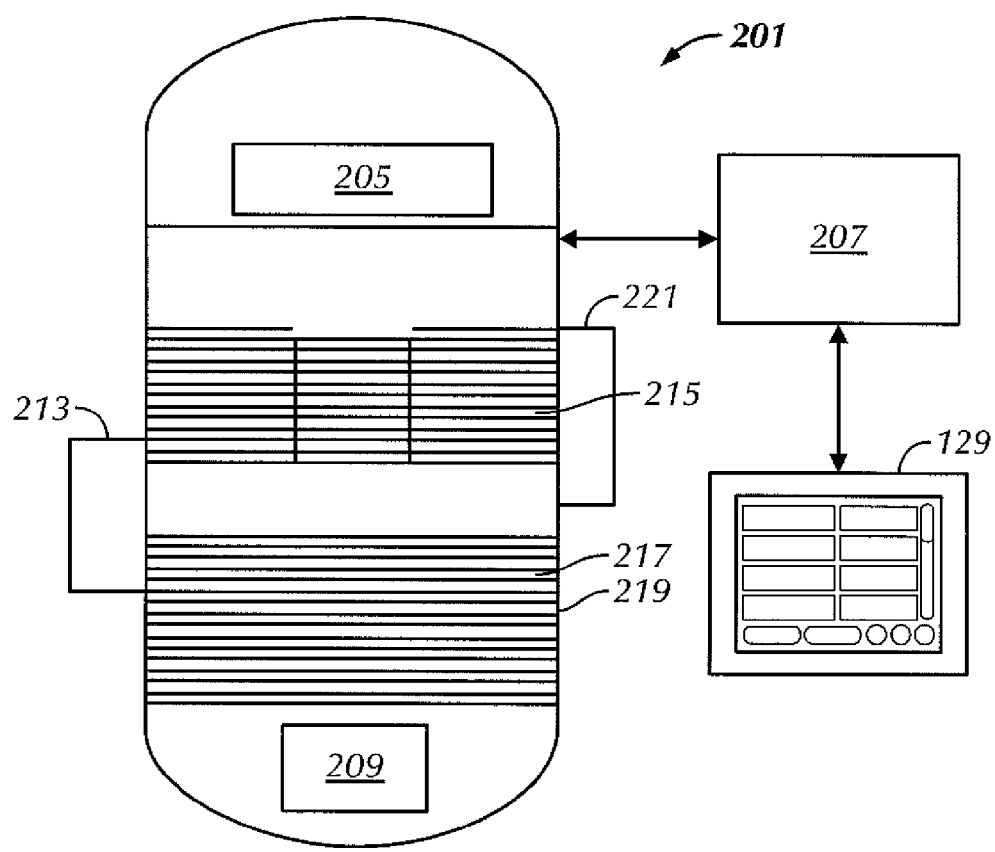
FIG. 2 shows a monitor module for monitoring asset health by dissolved gas measurement in accordance with one or more embodiments.

FIG. 2 shows one example of a monitor module in accordance with one or more embodiments. The monitor module 201 is mounted to an oil filled asset (not shown), as described above, by way of an adaptor 213. In accordance with one or more embodiments, the oil filled asset may be a piece of oil filled electrical equipment such as an oil filled transformer or LTC, or more generally, may be any piece of oil filled equipment. Adaptor 213 is adapted to mount to the oil filled asset in a number of asset specific configurations, as described in further detail below in reference to FIGS. 6-13. Furthermore, adaptor 213 includes plumbing for connecting the system 201 to the oil filled asset and also includes pumps, valves, sensors, etc., for extracting oil from the oil filled asset for dissolved gas analysis within the monitor module 201, as described in more detail below in reference to FIGS. 3-5. Monitor module 201 generally includes an electronics module 205 (optionally including NDIR dissolved gas analysis (DGA) system), an oil pump 209, and may further include optional inlet oil heating coils 215, inlet oil cooling coils 217, and outlet oil cooling coils 219.

In accordance with one or more embodiments, a monitor module 201 is powered by a stand-alone drive hub 207, i.e., monitor module itself does not include an internal power supply. Such a configuration beneficially removes the power supply and the communications electronics away from the heat that is typically associated with the monitor module 201 and may lead to poor performance or failure of the power supply. Furthermore, in accordance with one or more embodiments, the stand-alone drive hub 207 provides for single point connectivity for power and communications to a monitor module 201. In accordance with one or more embodiments, the stand alone drive hub 207 may include status indicators for each monitor module 201 that is connected.

Furthermore, in accordance with one or more embodiments, drive hub 207 is configured to supply electrical power to any or all of the electronics module 205, the oil pump 209, and indicator module 221. The electronics module 205 provides the necessary electronics for communication with and control of NDIR DGA system that may be integrated with or separate from the electronics module 205. The NDIR DGA system may include several electronic sensors, electronic valves, and an infrared gas detection system, e.g., a non-dispersive infrared ("NDIR") gas sensor. NDIR DGA subsystem is described in more detail below in reference to FIG. 3.

The indicator module 221 may include one or multiple indicators (e.g., a single large indicator light or a front panel including a bank of indicator lights, such as LEDs, or the like) for indicating to an outside observer the presence of various dissolved gases and also for indicating various fault conditions within the oil filled asset based on the amount detected of one or more gases dissolved in the oil in comparison with a preprogrammed threshold value.

In accordance with one or more embodiments, a monitor module 201 may be operably connected with and be able to exchange data with a controller 129 as described above. As described above, in accordance with one or more embodiments, the controller includes a touch screen interface. Furthermore in accordance with one or more embodiments, the drive hub 207 may communicate with the controller 129 by way of TCP/IP protocol thereby allowing the control to control a large number of drive hubs 207 easily by introducing them through a communication hub or switch, e.g., an RS485 multidrop hub or Ethernet hub connections. In accordance with one or more embodiments, the controller 129 may control a large number of, e.g. greater than 30, different drive hubs 207 and each drive hub 207 may drive two separate monitor modules. As shown in FIG. 1, in accordance with one or more embodiments, the drive hub 127 and/or the controller 129 and thereby any or all the monitor modules 201 may be accessed and/or controlled by way of a remote computing device such as a remote mobile device 131, e.g., a laptop, mobile phone, smart phone, tablet pc, or the like.

In accordance with one or more embodiments, the monitor module 201 may be connected through plumbing (not shown) within adaptor 213 to allow for the extraction of oil from the oil filled asset. The extracted oil then circulates through a fluid circulation loop, also referred to herein as the oil circulation loop, within the module 201 and is then returned to the oil filled asset. In accordance with one or more embodiments, the oil circulation loop may be a single loop, or may have a multi-loop design for isolation of the transformer tank from the separator membrane, as described in more detail below in reference to FIG. 4. In either of these configurations, the circulation and pressure of the oil in the oil circulation loop may be controlled by oil pump 209 mounted within one of or both of the oil circulation loop(s). According to other embodiments, the oil pump may be mounted within the adaptor itself, or according to further embodiments, two oil pumps may be utilized, one in the adaptor and one within analysis unit. Furthermore, in accordance with one or more embodiments, inlet oil heating coils 215, inlet oil cooling coils 217, and outlet oil cooling coils 219 are configured to control the temperature of the oil circulating through the oil circulation loop. Inlet heating coils 215 receive the oil extracted from the oil filled asset (not shown) and heat the oil to a predetermined temperature for gas transfer within the analysis unit, e.g. 40+/−10 C. Alternatively, inlet cooling coils 217 receive the oil extracted from the oil filled asset and remove heat from the oil to cool the oil to a predetermined temperature for optimal use within analysis unit. Furthermore, outlet cooling coils may be used to cool the oil before the oil is returned to the oil filled asset so that the oil may be returned to the oil filled asset at a temperature that does not inhibit the proper operation of the oil filled asset. While this example shows inlet oil heating coils 215, inlet oil cooling coils 217, and outlet oil cooling coils 219, any of these coils may be employed separately from all other coils depending on the conditions, e.g., a system may deploy only one heating coil, only one cooling coil, or any combination of coils without departing from the scope of the present disclosure.

Figure 3:
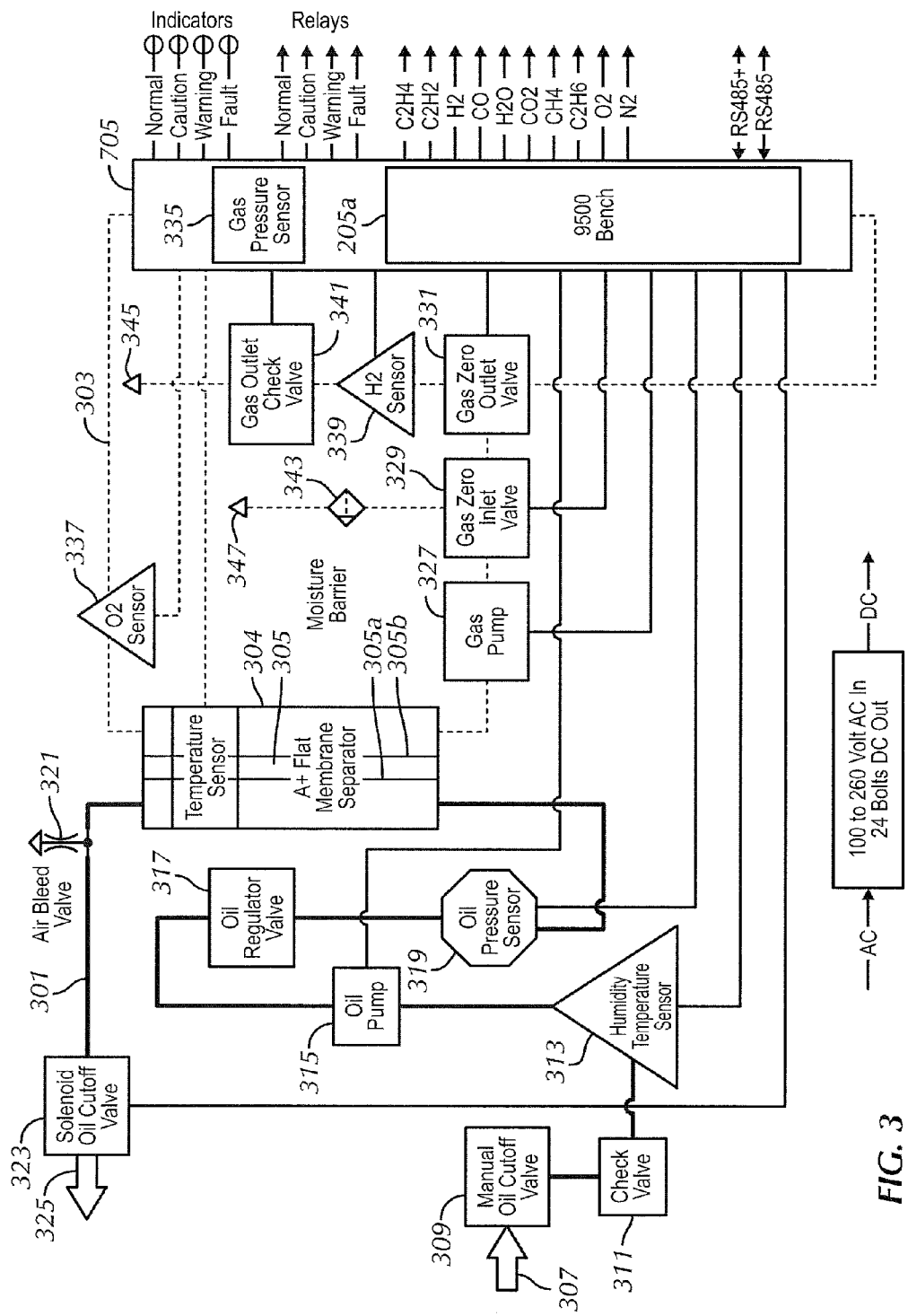
FIG. 3 shows a block diagram of a system for monitoring asset health by dissolved gas measurement in accordance with one or more embodiments.

FIG. 3 shows an example of the internal components of a monitor module capable of monitoring asset health by dissolved gas measurement in accordance with one or more embodiments. The monitor module includes at least two separately circulating fluid loops. In accordance with one or more embodiments, the first fluid loop 301 is the oil circulation loop configured to circulate oil extracted from the oil filled asset and the second fluid loop 303 is the gas circulation loop, configured to circulate gas extracted from the extracted oil. The first fluid loop and second fluid loop are coupled via a gas separator unit 304 including at least one gas permeable membrane 305. In accordance with one or more embodiments, the gas permeable membrane may be any gas permeable polymer membrane known in the art. Example polymer membranes that may be used include those sold by A+ Corporation (Gonzales, La.), e.g., the M120-5X6, or the like. Furthermore, in accordance with one or more embodiments, the membrane 305 may be sandwiched between two porous metal plates (not shown) in order to minimize pressure induced deflections in the membrane. The membrane described above may be employed in any or all of the embodiments disclosed below and is not limited to the arrangement shown in FIG. 3.

In accordance with one or more embodiments, gas that is initially dissolved in the oil circulating through the first fluid loop may be extracted by contacting one side 305a of the gas permeable membrane 305. The gas diffuses through the gas permeable membrane 305, thereby entering the second fluid loop, where the extracted gas is circulated separately within the second fluid loop. In accordance with one or more embodiments, the gas permeable membrane is substantially impermeable to the oil circulating within the first fluid loop and, thus, under normal operation, oil is kept from entering the second fluid loop and the dissolved gas is effectively separated from the oil for analysis by the monitor module. In accordance with one or more embodiments, the gas separator unit may employ a single planar gas permeable membrane. In other embodiments, the gas separator unit may employ two planar gas permeable polymer membranes.

In accordance with one or more embodiments, the flow of oil within the first fluid loop is described below in reference to FIG. 3. Oil from the oil filled asset is extracted through inlet 307, circulated through first fluid loop 301 and returned through outlet 325. A manual cutoff valve 309 is installed after the inlet 307 to allow for manual cutoff of the oil flow from the oil filled asset, e.g., to be used during installation, servicing of the analysis unit, or in case of emergency shutdown of the analysis unit. In accordance with one or more embodiments, several additional components may be installed along and/or within the first fluid loop. FIG. 3 shows a check valve 311, humidity/temperature sensor 313, oil pump 315, oil regulator valve 317, oil pressure sensor 319, gas separator 304, air bleed valve 321 and solenoid cutoff valve 323 are each installed downstream of the manual oil cutoff valve 309.

In accordance with one or more embodiments, the flow of gas within the second fluid loop is described below in reference to FIG. 3. Gas dissolved in the extracted asset oil enters the second fluid loop 303 from the first fluid loop 301 by way of diffusion through gas permeable membrane 305 mounted within the gas separator 304. The pressure and flow rate of the extracted gas circulating within the second fluid loop 303 is controlled by gas pump 327. In accordance with one or more embodiments, several additional components may be installed along and/or within the second fluid loop 303. FIG. 3 shows gas zero inlet valve 329, a gas zero outlet valve 331, an electronics module/DGA subsystem 205, gas pressure sensor 335, oxygen ($O_2$) sensor 337, and gas separator 304.

In accordance with one or more embodiments, gas pump 327 circulates the extracted gas through electronics module 205 where the specific gas signature, i.e., mixture, may be identified. For example, electronics module 205 may employ an NDIR gas detection system for detecting various gases, e.g., $C_2H_4$, $C_2H_2$, $H_2$, CO, $H_2O$, $CO_2$, $CH_4$, $C_2H_6$, $O_2$, and $N_2$. In accordance with one or more embodiments, the extracted gas is provided to the instrument in a periodic, discontinuous fashion in order to insure that a minimal sample is utilized for analysis. In other words, the gas is introduced into the NDIR instrument sample pathway only at predefined, periodic intervals. Introducing the minimal sample to the NDIR instrument in the above manner ensures that gas in the second fluid loop remains in equilibrium with the gas in the first fluid loop, thus, improving measurement accuracy and repeatability. In accordance with other embodiments, gas is continuously circulated through the gas loop such that the sample pathway within the NDIR instrument is part of the gas loop. Accordingly the sample pathway becomes part of a gas equilibrium loop and the NDIR instrument may accurately measure the gas concentration at specific periodic intervals.

The second fluid loop 303 also includes a system for purging the second fluid loop with air, or other purge gas. This air purge allows for the NDIR instrument to be periodically calibrated and/or zeroed, before and/or after each measurement, when necessary. During a purge operation, air is introduced into the system through inlet 347, via the gas zero inlet valve 329. Before entering the system, the air is passed through moisture barrier 343 to remove water vapor. The air is then returned to the atmosphere by way of gas zero outlet valve 331 and gas outlet check valve 341. Gas outlet check valve 341 is connected so as to ensure that under normal operating conditions, air may not enter the system through outlet 345. In addition, in accordance with one or more embodiments, hydrogen sensor 339 may be mounted between the gas zero outlet valve 331 and gas outlet check valve 341.

Electronics module 205 further includes the necessary electronics for control and communication with the various pumps and sensors of the monitor module. In accordance with one or more embodiments, the electronics module 205 includes electronics bench 205a which provides control and communication lines to control and communicate with solenoid oil cutoff valve 323, humidity/temperature sensor 313, oil pump 315, oil pressure sensor 319, gas pump 327, gas zero inlet valve 329, gas zero outlet valve 331, $H_2$ sensor 339, gas outlet check valve 341, and $O_2$ sensor 337. The electronics bench 205a may be employed using the DGA platform available from Lumasense, marketed as the ANDROS 9500 multi-gas platform. Alternatively, any known multi-channel gas detection platform may be used. One of ordinary skill will appreciate that any number of alternate configurations of sensors and control lines may be implemented in accordance with one or more embodiments, and, thus, the particular arrangement shown in FIG. 3 is not meant to limit the scope of the present disclosure.

In accordance with one or more embodiments, FIG. 3 illustrates one possible configuration of pumps, sensors, and control lines that may facilitate the precise control of the pressure differential applied across the membrane. As used herein, the pressure differential is defined to be the difference between the pressure applied to side 305a and 305b of the membrane 305. Further, the pressure differential may be affected and/or controlled by controlling the pressure in the first and second fluid loops, (i.e., the oil and the gas loops, respectively). Thus, as used herein, the concept of controlling the pressure differential across the membrane may encompass directly or indirectly modifying the pressure being applied to either of side 305a and 305b of the membrane. For example, the pressure applied to side 305a may be controlled via oil pump 315 that is controlled by control line that originates from electronics bench 205a. The control signal sent to oil pump 315 from electronics bench 205a may depend on the pressure reading from oil pressure sensor 319, as compared to a predetermined pressure set point. Similarly, the pressure applied to side 305b may be controlled via gas pump 327 that is controlled by control line that originates from electronics bench 205a. The control signal sent to gas pump 327 from electronics bench 205a may depend on the pressure reading from gas pressure sensor 335, as compared to a predetermined pressure set point. Accordingly, the pressure across the membrane may be controlled to a predetermined pressure differential by control of one of or both of gas pump 327 and oil pump 315. Furthermore, the pumps may be controlled by electronics bench 205a based on the pressures within the two fluid loops, for example, as measured by oil pressure sensor 319 and gas pressure sensor 335.

For example, in accordance with one or more embodiments, the pressure in the oil loop may be controlled to be +/−0.5 psi above the pressure in the gas loop, thus, providing a suitable pressure differential across the membrane 305. One of ordinary skill will appreciate that the precise value of the predetermined pressure differential may depend on many factors including oil temperature, dissolved gas concentration, gas separator design, e.g., single membrane or multiple membrane design.

Figure 4:
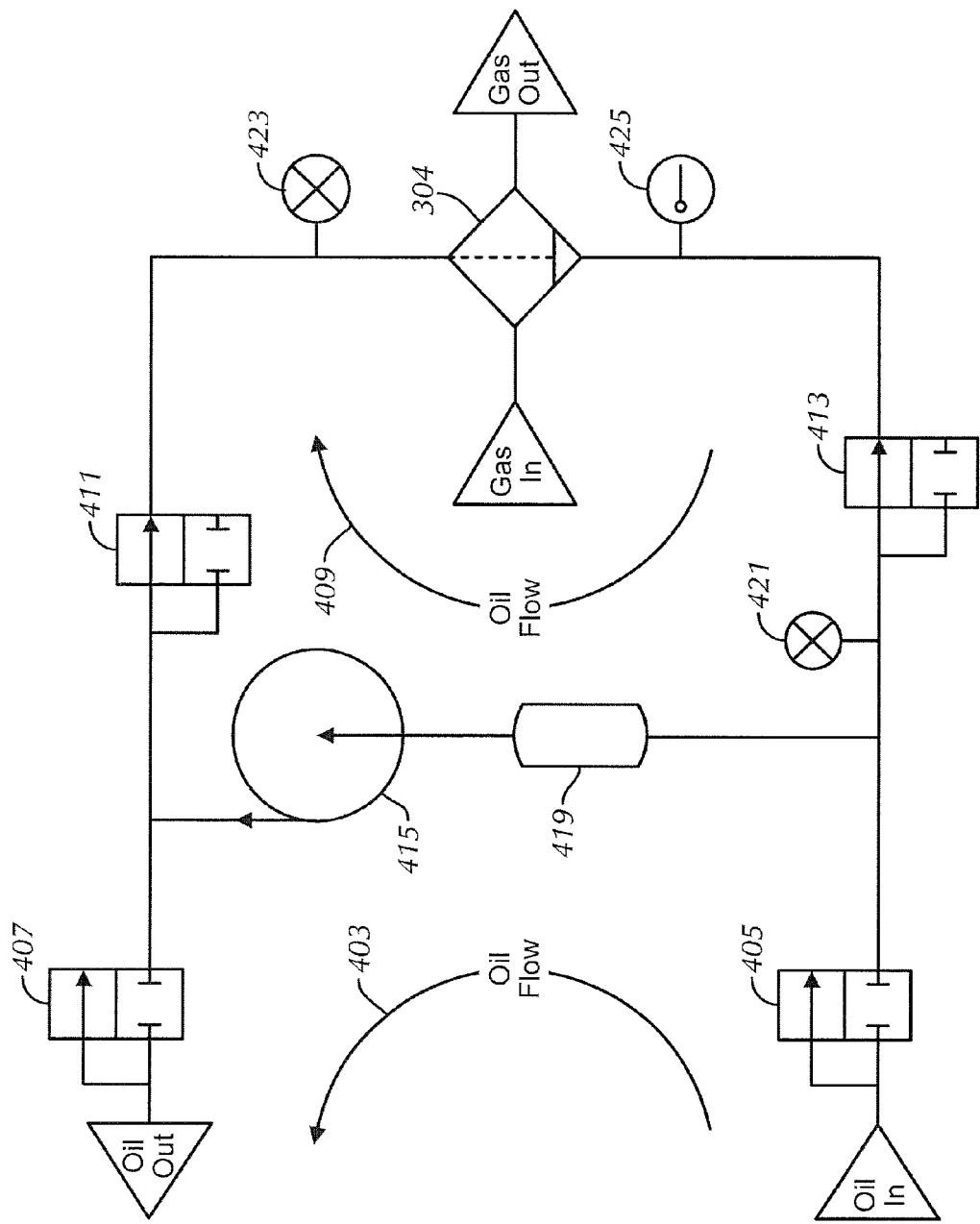
FIG. 4 shows an example of an oil loop in accordance with one or more embodiments.

FIG. 4 shows an example of an oil loop within a monitor module in accordance with one or more embodiments. In the example shown in FIG. 4, the oil loop includes two separate loops to allow for isolation of the gas separator 304 from the oil filled asset. The separation is accomplished through the use of four solenoid valves, two in an asset oil loop 403, i.e., solenoid valves 405, 407 and two in an oil circulation loop 409, i.e., solenoid valves 411, 413. The isolation of the gas separator 304 from the oil filled asset is accomplished as follows. During installation all four solenoid valves are closed. Once installed, solenoid valves 405 and 407 are opened, thereby allowing the oil pump 415 to circulate oil in asset oil loop 403. Furthermore, as oil circulates, temperature controlled oil reservoir 419 is filled with oil from the asset. In accordance with one or more embodiments, the temperature controlled oil reservoir 419 is heated by heaters, e.g., resistive heaters, and cooled passively by way of cooling coils. In accordance with one or more embodiments, the temperature of the oil may be maintained at 40+/−10 C and the capacity of the reservoir may be approximately 3.5 ml. However, the precise temperature and capacity may change depending on the viscosity of the oil and the solubility of the various gasses being monitored. Accordingly, any temperature and capacity may be used without departing form the scope of the present disclosure.

Once the temperature controlled oil reservoir 419 is filled, pump 415 is turned off and valves 405 and 407 are closed. Then valves 413 and 411 are opened, and pump 415 is turned back on, resulting in oil now circulating within oil loop 409, thereby exposing gas separator 304 to the circulating oil under test. Advantageously, this four valve configuration allows for at least two valves to always be isolating the asset internal oil volume from the gas separator 304. This isolation eliminates the risk of rupture of the membrane of gas separator 304 due to uncontrolled pressure fluctuations (both over and under pressure) at the inlet or outlet due to changing conditions in and around the oil filled asset. Furthermore, as shown in FIG. 4, a number of pressure sensors, e.g., pressure sensors 421 and 423 may be used to monitor the pressure in the two oil loops to ensure the pressure is properly controlled in a manner similar to that described above in reference to FIG. 3. Furthermore, a humidity and temperature sensor 425 may be used within the oil loop 409.

In accordance with one or more embodiments, the pressure differential across the membrane(s) of gas separator 304 is controlled by the oil pump even when the instrument is in the idle state, i.e., even when DGA measurements are not being taken. Advantageously, this assures that the membrane(s) will not be inadvertently damaged due to, e.g., temperature swings in the oil due to changing environmental conditions (the pressure is strongly dependent on the temperature of the oil). Furthermore, stabilization of the pressure and temperature ensures that equilibrium is always maintained across the membrane, thereby increasing accuracy and reducing the time required to make a dissolved gas measurement.

Figure 5:
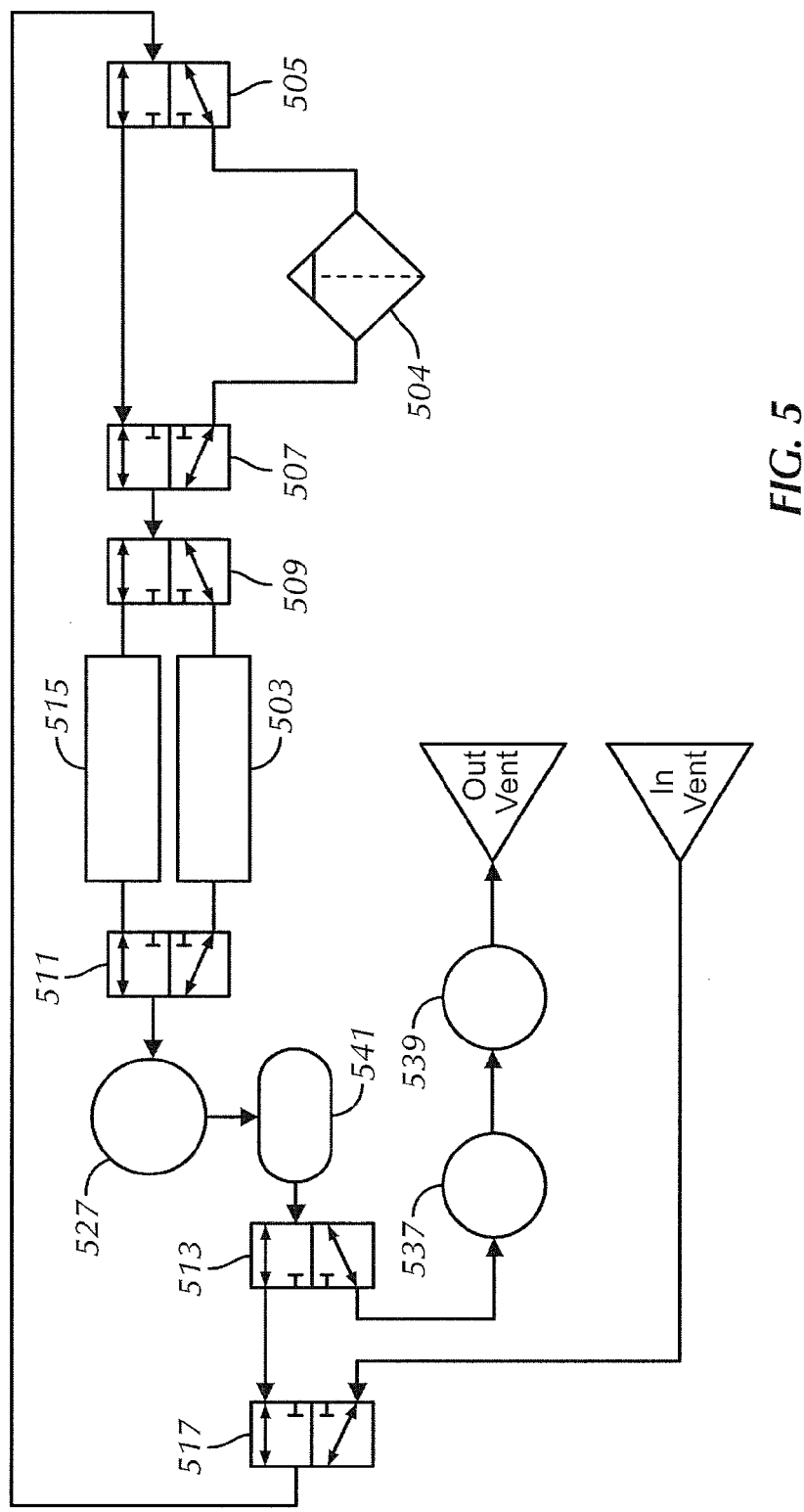
FIG. 5 shows an example of a gas loop in accordance with one or more embodiments.

FIG. 5 shows an example of a gas loop within a monitor module in accordance with one or more embodiments. Functionally, the gas loop shown in FIG. 5 is similar to that shown in FIG. 3 in that it includes a system for circulating a gas through an NDIR instrument, where the gas is introduced into the loop by diffusion through the membrane separator 504. In this example, measurements are made as the gas is circulated through a sample cell 503, that, e.g., may be partially housed within a DGA instrument. Furthermore, like the loop shown in FIG. 3, the loop shown in FIG. 5 includes $H_2$ sensor 539 and $O_2$ sensor 537. Also like the example shown in FIG. 3, the loop shown in FIG. 5 includes a gas pump 527 that is fluidly connected to the sample cell 503 through a series of pipes and valves. As shown in FIG. 5, in this example, the valves 505, 507, 509, 511, 513, and 517 are all X-valves that allow for measurement and purge operations as described above in reference to FIG. 3. However, the embodiment shown in FIG. 5 differs from FIG. 3 in that FIG. 5 shows a more detailed view of an NDIR instrument that includes both a sample chamber 503 and an adjustable volume chamber 515. As can be seen from the drawing, X-valves 509 and 511 are configured to allow the adjustable volume cell 515 to be part of the overall sample containing chamber thereby allowing the choice of filling both the adjustable volume cell 515 and the sample chamber 503 of filling up either. Filing up both cells in some cases is beneficial for acquiring enough gas to make a reliable $H_2$ measurement at $H_2$ sensor 539, depending on the type of sensor used. In accordance with one or more embodiments, solid state gas sensors are used for both $H_2$ sensor 539 and $O_2$ sensor 537, for example sensors of the type manufactured by Figaro (Arlington Heights, Ill.). However, any sensor may be used without departing from the scope of the present disclosure. Another advantageous aspect of the adjustable volume 515 configured as shown in FIG. 5 is that the adjustable volume 515 may be used to bypass, or short circuit the sample path. Thus, the entire gas pathway may be purged without affecting the contents of the sample cell 503. In accordance with one or more embodiments, the gas pathway also includes a humidity sensor 541.

Figure 6:
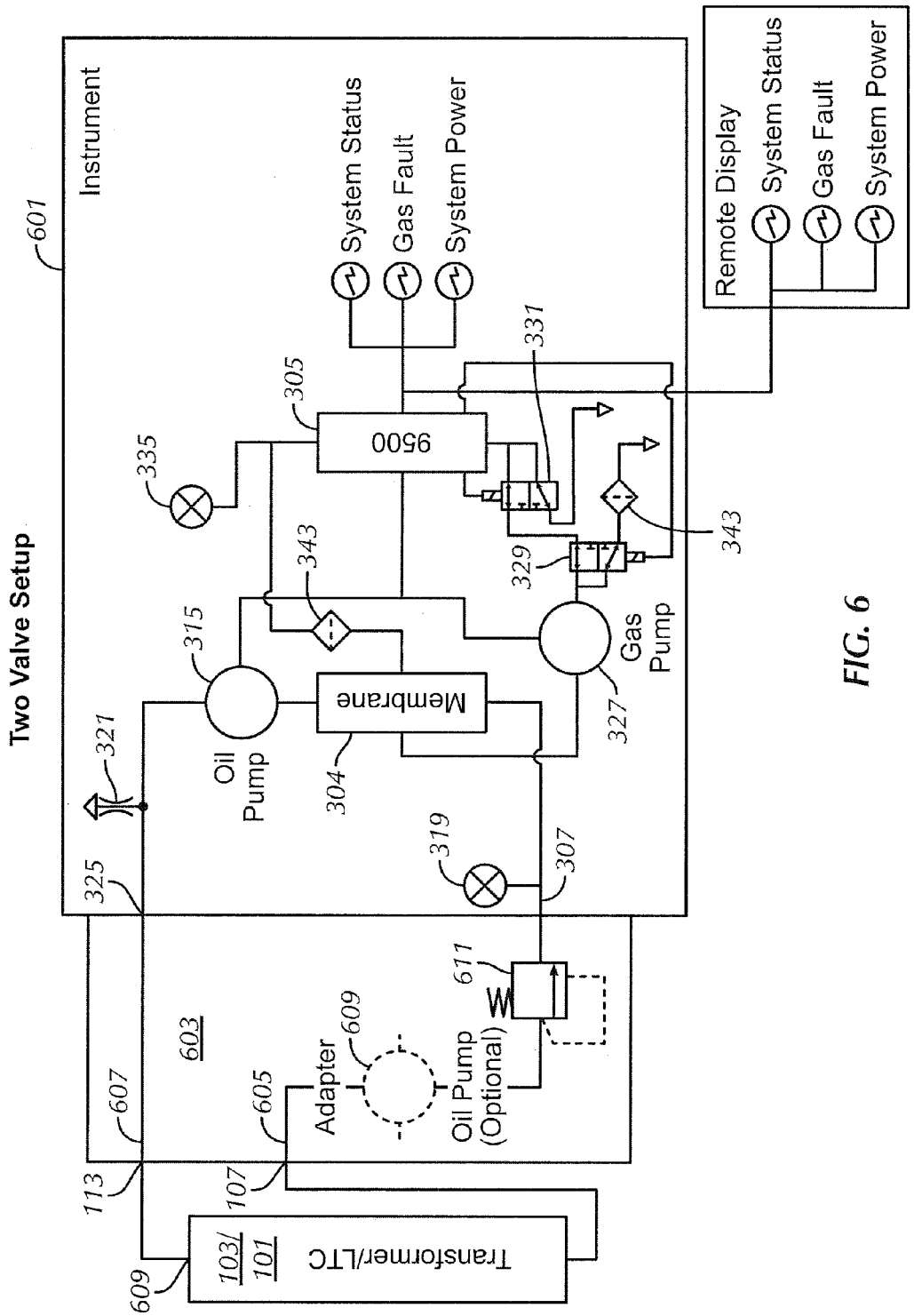
FIG. 6 shows a block diagram of a two-valve installation of a system for monitoring asset health by dissolved gas measurement in accordance with one or more embodiments.

FIG. 6 shows the system for monitoring asset health by dissolved gas measurement and adaptor 603 for mounting the system in the two-valve configuration in accordance with one or more embodiments. As shown in FIG. 6, the adaptor 603 includes inlet 605 and outlet 607 for extracting and returning asset oil from the oil drain valve 107 and oil fill valve 113 respectively (See also FIG. 1). Also optionally included within adaptor 603 is secondary oil pump 609 and pressure regulator 611. In accordance with one or more embodiments, secondary oil pump 609 may facilitate the pumping of oil up to the height of oil fill inlet, which may be upwards of 10-15 vertical feet above ground level, for return to a transformer main tank. In other embodiments, the secondary oil pump 609 is not necessary and is therefore not present in the system. For convenience, elements within instrument 601 common to FIGS. 1-3 are labeled with common numbers.

Figure 7:
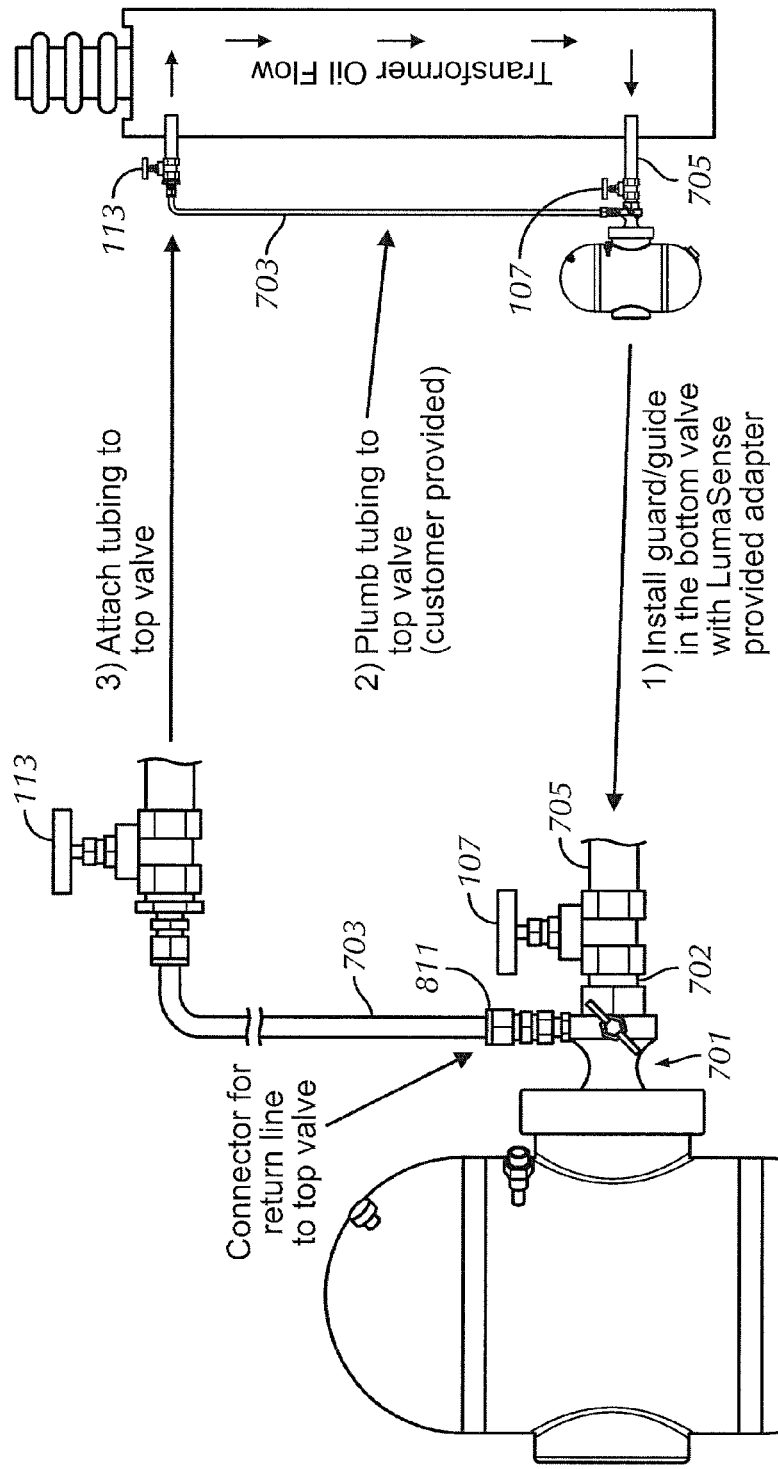
FIG. 7 shows a two-valve installation of a system for monitoring asset health by dissolved gas measurement in accordance with one or more embodiments.

FIG. 7 shows an example of the two valve configuration in accordance with one or more embodiments. More specifically, FIG. 7 shows a configuration wherein adaptor 701 is connected to both transformer fill line 703 and transformer drain line 705, the so-called two valve configuration. In this example, adaptor 701 includes a front end threaded connection 702 so that the adaptor may thread directly into oil drain valve 107. Furthermore, the back end of adaptor 701 includes a flange that is configured to attach to a monitor module. Accordingly, when using this adaptor, the monitor receives oil from transformer drain line oil valve 107 and returns oil to the transformer by way of oil fill valve 113 and oil sample return port 811.

Figure 8:
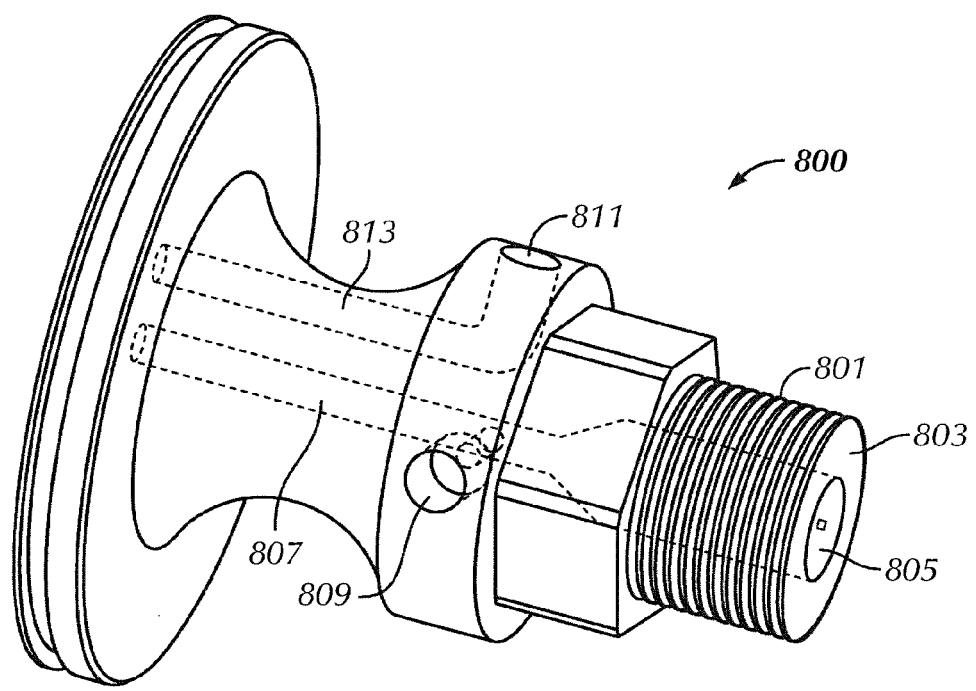
FIG. 8 shows an adaptor for a two-valve installation in accordance with one or more embodiments.

FIG. 8 shows a more detailed view of the adaptor for two-valve configuration. In accordance with one or more embodiments, the adaptor 800 includes a front threaded portion that is able to be threaded into a transformer valve, e.g., at the transformer drain line oil valve. Furthermore, the front face 803 of adaptor 800 includes an oil sample input port 805 that is fluidly connected to an input internal passage 807 of the adaptor. This input internal passage 807 corresponds to inlet 605 as shown in FIG. 6 and is also fluidly connected to the inlet of the monitor module (e.g., inlet 307 shown in FIG. 3). Furthermore, the adaptor 800 includes a sample bleed port 809 that includes a bleeder valve (not shown) for bleeding oil and/or air from the system. Adaptor 800 further includes oil sample return port 811 for receiving the transformer fill line 703. Oil sample return port 811 is fluidly connected to output internal passage 813 that may be displaced from (adjacent to) the input internal passage 807. The rear portion of the adaptor 800 is configured to mate with the front face of a monitor module (not shown). This mating may be accomplished by any way known in the art, e.g., by an array of screws.

FIG. 9 shows the system for monitoring asset health by dissolved gas measurement and adaptor 903 for mounting the system in the single valve probe configuration in accordance with one or more embodiments. As shown in FIG. 9, the adaptor 903 includes inlet 905 and outlet 907 both originating from within probe 913 which extracts and returns asset oil from an oil filled asset, e.g., the LTC valve 115 or transformer drain valve 107. As shown in FIG. 9, the adaptor 903 includes a probe 913 that may be inserted into a single valve, e.g., valve 115 and/or valve 107 shown in FIG. 1. Furthermore, in accordance with one or more embodiments, the probe is configured in a dual passage geometry, shown in more detail in FIGS. 10-11, that includes an oil inlet passage 1005 through which oil from the asset is extracted and an oil outlet passage 1007 through which fluid is returned to the asset. Advantageously, using this adaptor, oil is extracted and returned through a single valve. Also optionally included within adaptor 903 is secondary oil pump 909 and pressure regulator 911. In accordance with one or more embodiments, secondary oil pump 909 may facilitate the pumping of oil up to the height of the LTC valve 115. In other embodiments, the secondary oil pump 909 is not necessary and is therefore not present in the system. For convenience, elements within instrument 901 common to FIG. 1 are labeled with common numbers.

FIG. 10 shows an example of a probe adaptor in accordance with one or more embodiments. More specifically, the probe adaptor 1000 shown in FIG. 10 includes a retractable probe member 1001 that is slidably engaged within a hole in a threaded input portion 1011. The threaded input portion 1011 may be threaded into the output port a single valve (not shown), e.g., valve for monitoring the oil from an LTC. Furthermore, the retractable probe member 1001 may be cut to length depending on the size of the valve and the size of the transformer tank. The output end 1103 of the retractable probe member 1001 is fluidly connected to an input internal passage 1005 that is, in turn, fluidly connected to an inlet of a monitor module (not shown). Furthermore, an output internal passage 1007 connects the outlet of the monitor module to an output port 1009 of the threaded input portion 1011. Accordingly, when the probe adaptor 1000 is mounted onto an oil filled asset by way of a single valve, the output port 1009 will discharge oil leaving the monitor module into the annular region within the valve that surrounds the retractable probe member 1001. Thus, the input and output ports form a dual passage structure within the combination created by the threaded input portion 1011 and the module coupler 1107. Advantageously, this retractable probe configuration allows for a monitor module to be attached to an oil filled asset by way of a single valve. Also due to the customizability of the length of the retractable probe member 1001, oil may be drawn from a position inside the asset that, is spatially separated from the return port of the adaptor, thereby ensuring that the probe draws a new oil sample for monitoring rather than drawing oil just discharged from the output port 1009.

Figure 11A:
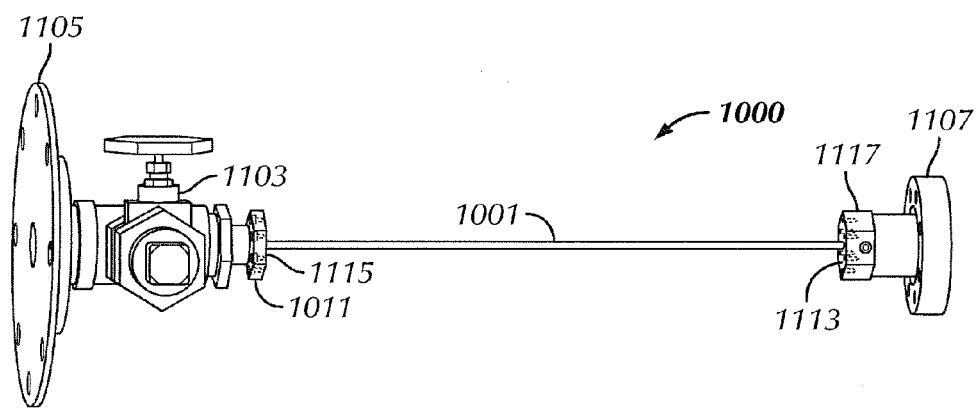
FIGS. 11A-11B show an example of an adaptor for a single valve installation in accordance with one or more embodiments.
Figure 11B:
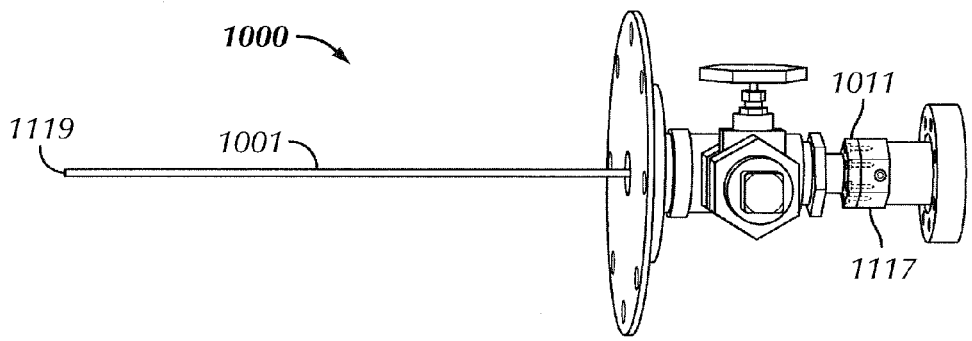

FIGS. 11A-11B show examples of the probe adaptor 1000 in a retracted configuration and an engaged configuration, respectively, in accordance with one or more embodiments. In this example, valve 1103 may be a valve that is connected to an oil filled asset by way of a coupler 1105. In the example shown in FIG. 11A, the coupler is a circular plate that may be bolted or screwed into an outer wall oil filled asset, e.g., a transformer and/or LTC tank wall. The valve 1103 is then threaded into the coupler to join the valve 1103 to the tank. Of course, the coupler shown here is merely an example and any type of coupler may be used without departing from the scope of the present disclosure. The probe adaptor itself includes the threaded input portion 1011 and the retractable probe member 1001. The output end 1117 of the retractable probe member 1001 is fixed to a module coupler 1107 that is configured to couple the adaptor 1000 to a monitor module (such as that shown in, e.g., FIG. 1). In accordance with one or more embodiments, the retractable probe member 1001 joined with the module coupler 1107 are able to slide into and out of the threaded input portion 1011 as a single unit to allow the input end 1119 of the retractable probe member 1001 to be positioned inside the asset being monitored.

FIG. 11A shows the probe adaptor 1000 in a fully retracted configuration as would be the case during installation of the adaptor. Once threaded input portion 1011 is threaded into the valve 1103, the retractable probe member 1001 is then inserted into the asset until it reaches a full engaged position as shown in FIG. 11B. In the engaged position, the face 1113 of module coupler 1107 seals against the face 1115 of the threaded input portion 1011 so that no oil is allowed to escape. In accordance with one or more embodiments, the module coupler 1107 and threaded input portion 1011 are drawn together using an array of bolts or screws. One of ordinary skill will appreciate that many different methods of sealing two surfaces are known in the art and accordingly any known method may be used without departing from the scope of the present disclosure. One of ordinary skill will also appreciate that one or both of the surfaces may be configured to house an O-ring or gasket.

Figure 34:
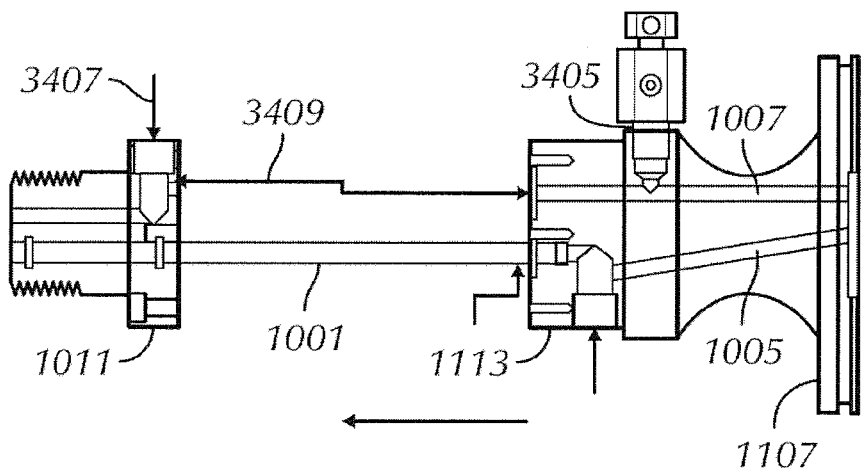
FIG. 34 shows an example of an adaptor for a single valve installation in accordance with one or more embodiments.

FIG. 34 shows a cross-sectional view of a probe adaptor in a partially retracted configuration. In particular, FIG. 34 shows the dual passage structure found within the module coupler 1107. Shown within the module coupler is a portion of oil inlet passage 1005 through which oil from the asset is extracted and an oil outlet passage 1007 through which fluid is returned to the asset. Also shown in FIG. 34 are two isolation valves 3407 and 3405 for isolating oil inlet passage 1005 and oil outlet passage 1007. In addition, isolation valve 3407 may be used to isolate the output portion of outlet passage 1007 from the transformer or LTC oil tank. Path 3409 shows roughly the oil return path (assuming the probe is in the engaged position), while retractable probe member 1001 in combination with oil inlet passage 1005 forms the input oil pathway. In accordance with one or more embodiments, retractable probe member 1001 may be formed of stainless steel tube, or the like.

Figure 12:
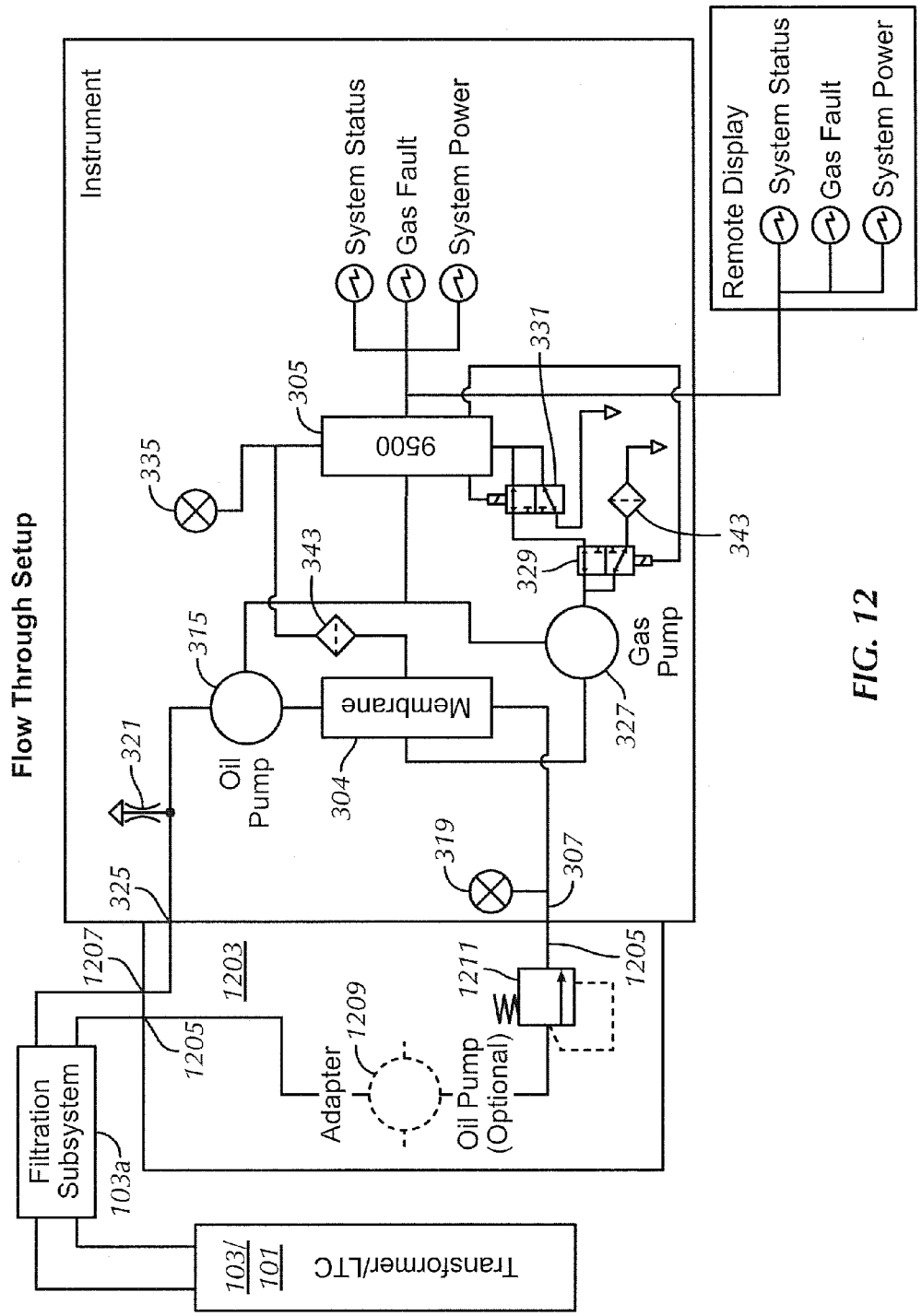
FIG. 12 shows a block diagram for a flow through installation of a system for monitoring asset health by dissolved gas measurement in accordance with one or more embodiments.

FIG. 12 shows the system for monitoring asset health by dissolved gas measurement and adaptor 1203 for mounting the system in the flow through configuration in accordance with one or more embodiments. As shown in FIG. 12, the adaptor 1203 includes inlet 1205 and outlet 1207 for extracting and returning asset oil from the oil filtration subsystem 103a. Also optionally included within adaptor 1203 is secondary oil pump 1209 and pressure regulator 1211. In accordance with one or more embodiments, secondary oil pump 1209 may facilitate the pumping of oil up to the height of the filtration subsystem for return to a transformer main tank. For convenience, elements within instrument common to FIG. 1 are labeled with common numbers. In other embodiments, the secondary oil pump 1209 is not necessary and is therefore not present in the system.

FIGS. 13A and 13B show an example of flow through configuration and a flow through adaptor in accordance with one or more embodiments. Shown in FIGS. 13A and 13B is an LTC oil filtration system 1303 of the type used in transformers in the power industry. Accordingly, the system 1303 generally includes known filters, pumps, power supplies, etc. In accordance with one or more embodiments, a flow through adaptor 1305 may be inserted into one of the flow lines 1309 of the oil filtration system 1303 so as to divert the oil to a monitor module 1307 for monitoring the dissolved gas in the oil, as described above. Furthermore, the monitor module 1307 itself may be attached to a two port monitor adaptor 1311 similar to that shown in FIG. 8, except that in this case, an input port 1313 and an output port 1315 leading to an inner input passage and an inner output passage, respectively, are located in the adaptor. Furthermore, the two port monitor adaptor may include a valve 1317 for isolating the monitor module from the system. The flow through adaptor 1305 thus diverts oil being pumped through flow line 1309 of the oil filtration system to input line 1319 of the monitor module 1307. Input line 1319 the monitor module 1307 connects to the inner input passage (not shown) of the two port monitor adaptor 1311. The oil is then directed into an inlet of the monitor module 1307, in a manner similar to that shown in FIG. 12. The oil is then monitored for dissolved gases, as described above. Oil is returned to the filtration system by way of a fluid path defined by a monitor outlet (e.g., outlet 325 in FIG. 12), an adaptor outlet port 1315, return line 1321. An example of a flow through adaptor is shown in FIG. 13B.

Figure 14:
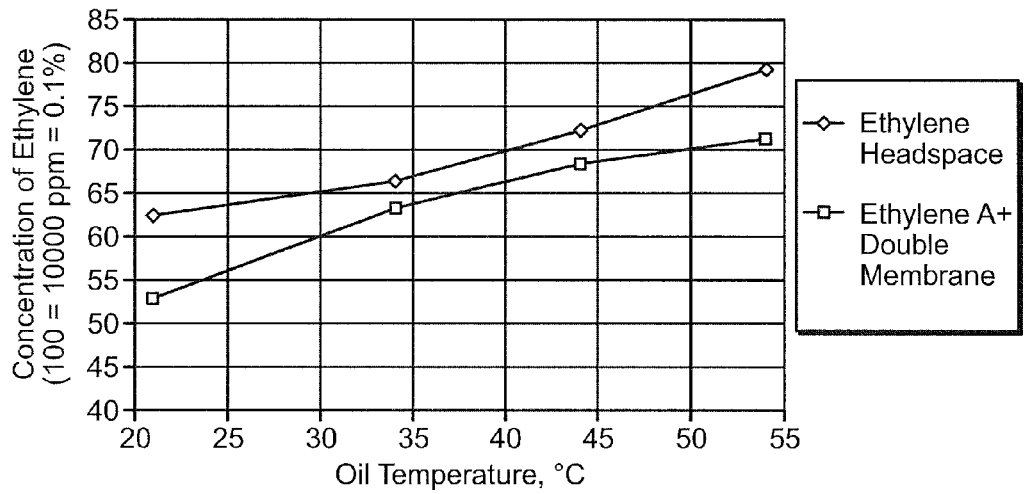
FIG. 14 shows test data in accordance with one or more embodiments.

FIG. 14 shows test results from the system for monitoring asset health by dissolved gas measurement in accordance with one or more embodiments. The plot shows the result of the system measuring ethylene in a closed oil filled system across different temperature ranges (e.g., 20 to 55 C).

Figure 15:
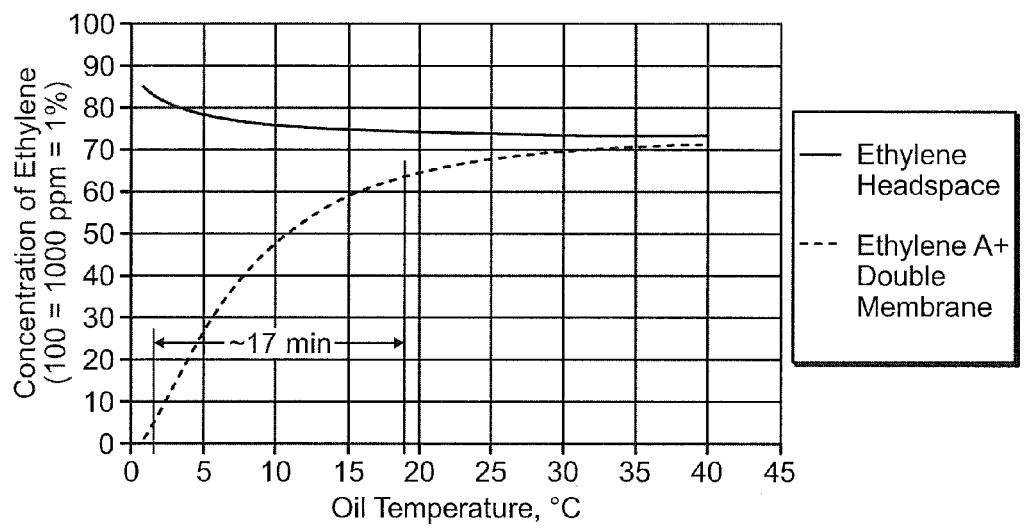
FIG. 15 shows test data in accordance with one or more embodiments.

FIG. 15 shows test results from the system for monitoring asset health by dissolved gas measurement in accordance with one or more embodiments. The plot shows the dynamic performance of the system, i.e., the time to reach a steady state response. The example is shown for ethylene, which reaches steady state in 17 minutes for this test.

Figure 16:
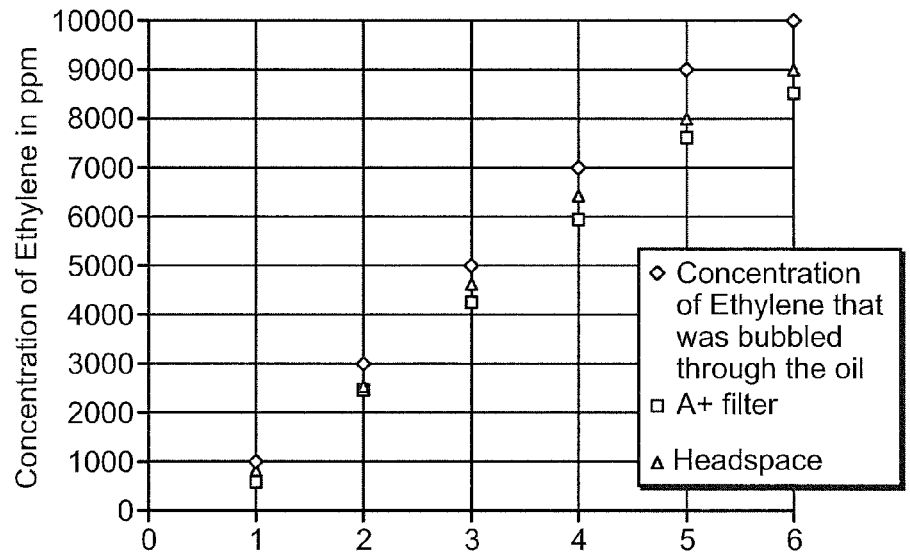
FIG. 16 shows test data in accordance with one or more embodiments.

FIG. 16 shows test results from the system for monitoring asset health by dissolved gas measurement in accordance with one or more embodiments. The plot shows the comparison of the system with the known method of headspace extraction that is an accepted IEEE standard. An example of the calibration curve of ethylene from 0 to 10,000 ppm is showing correlation between the system in accordance with one or more embodiments and the headspace method.

Figure 17:
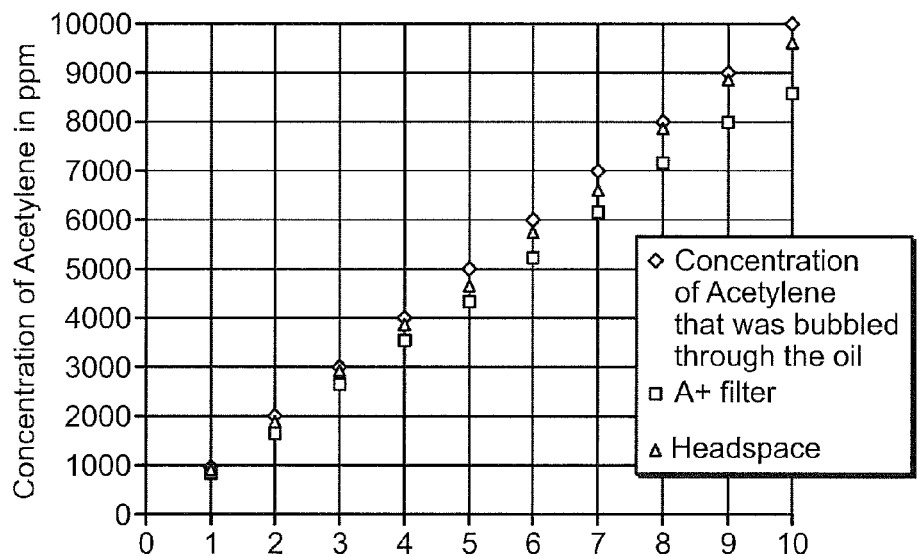
FIG. 17 shows test data in accordance with one or more embodiments.
Figure 19:
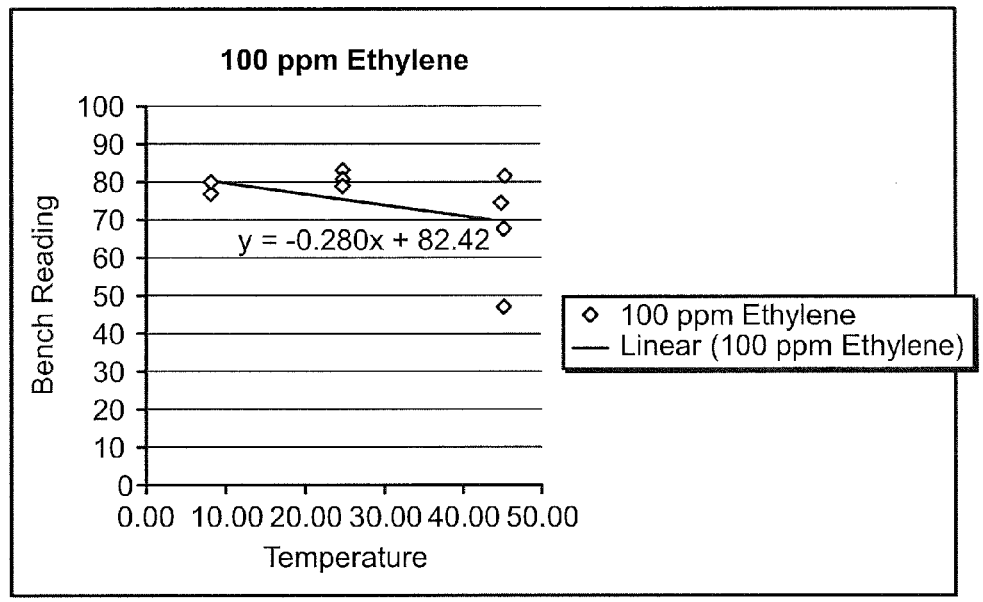
FIG. 19 shows test data in accordance with one or more embodiments.
Figure 20:
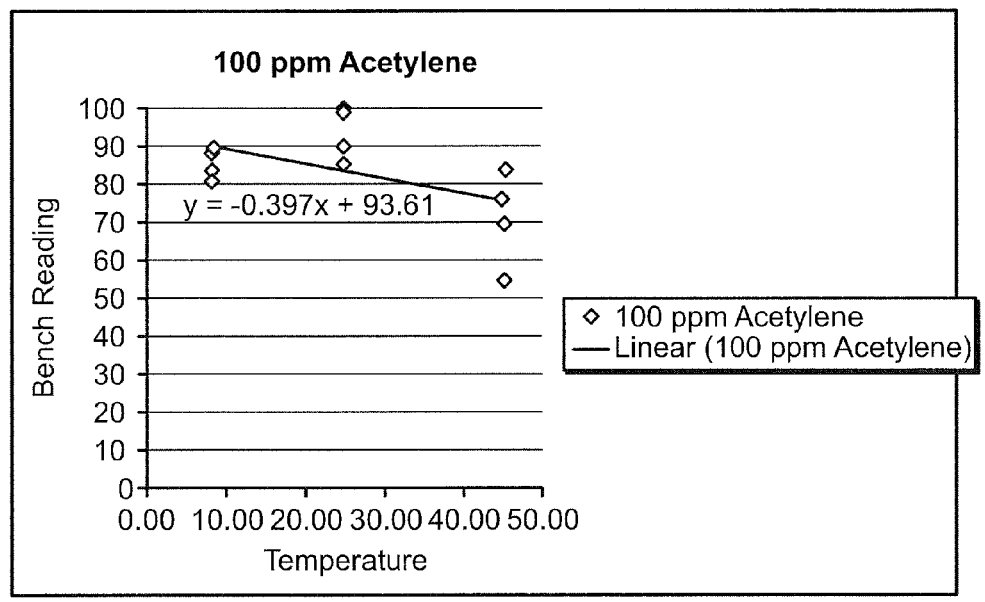
FIG. 20 shows test data in accordance with one or more embodiments.
Figure 21:
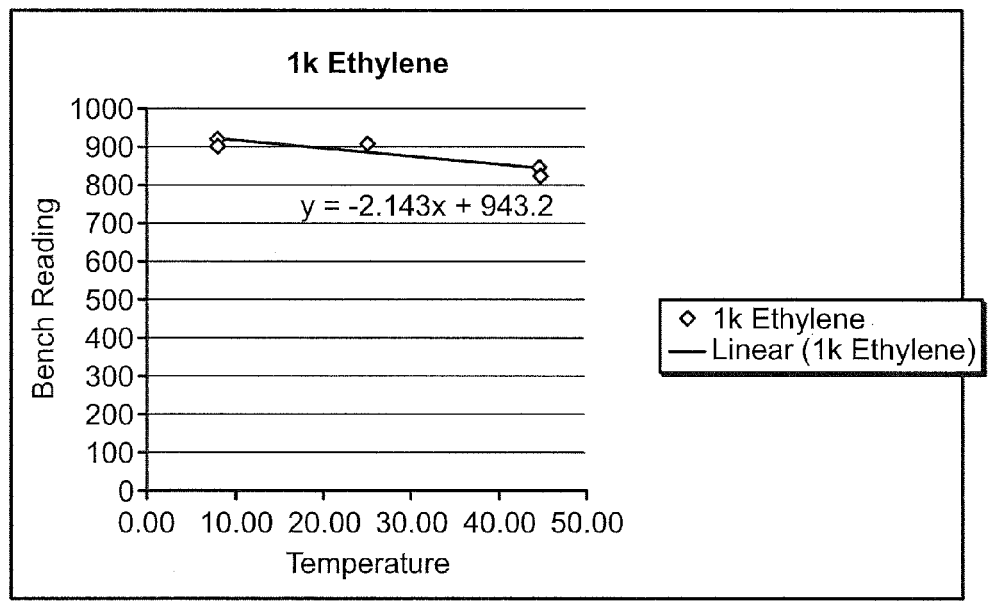
FIG. 21 shows test data in accordance with one or more embodiments.
Figure 22:
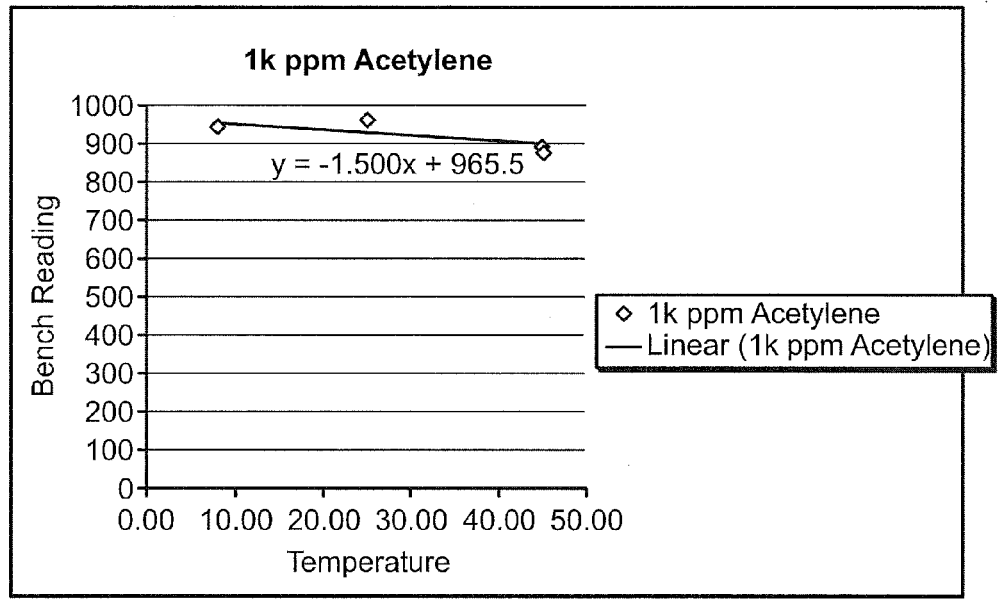
FIG. 22 shows test data in accordance with one or more embodiments.
Figure 23:
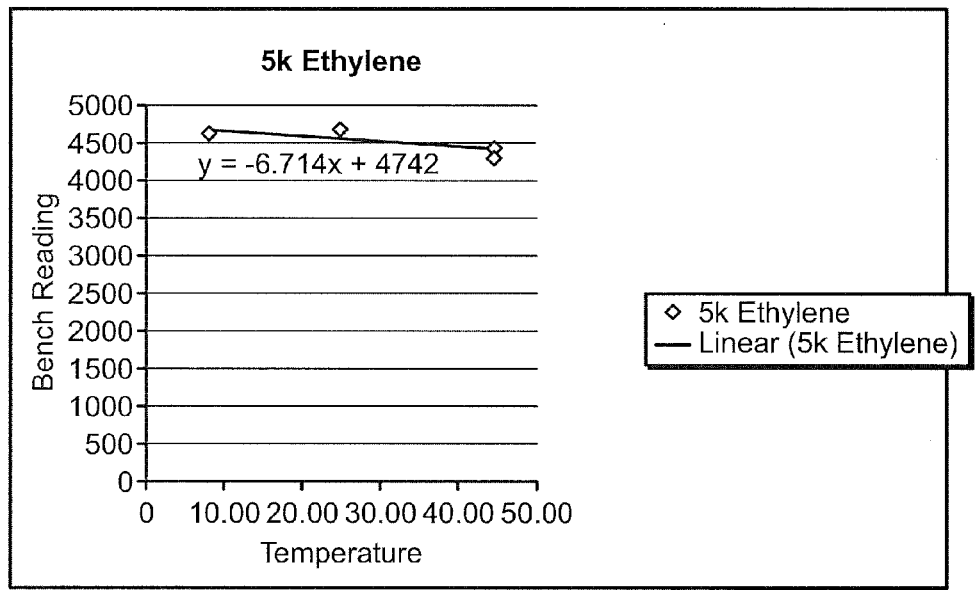
FIG. 23 shows test data in accordance with one or more embodiments.
Figure 24:
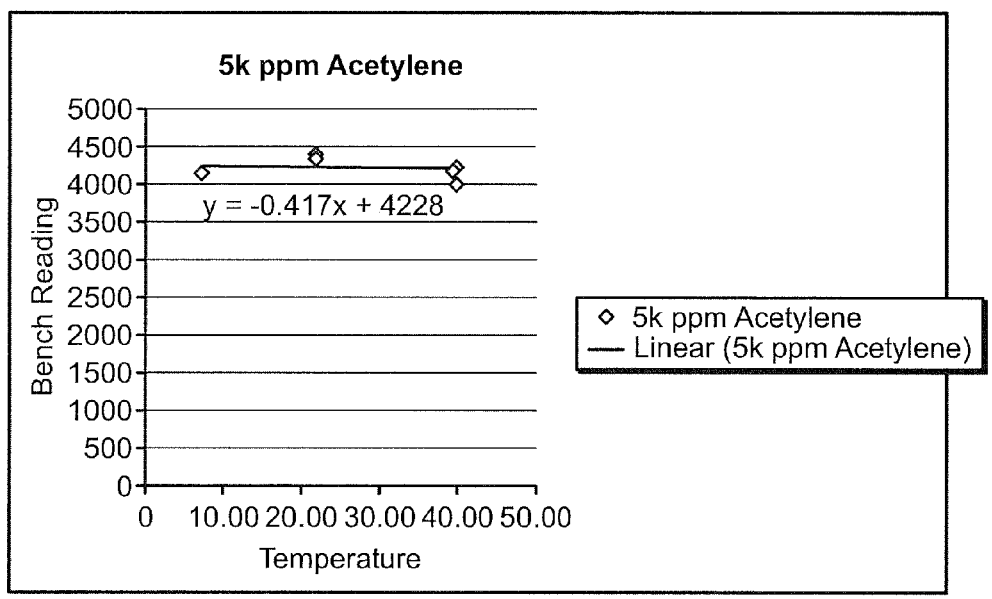
FIG. 24 shows test data in accordance with one or more embodiments.
Figure 25:
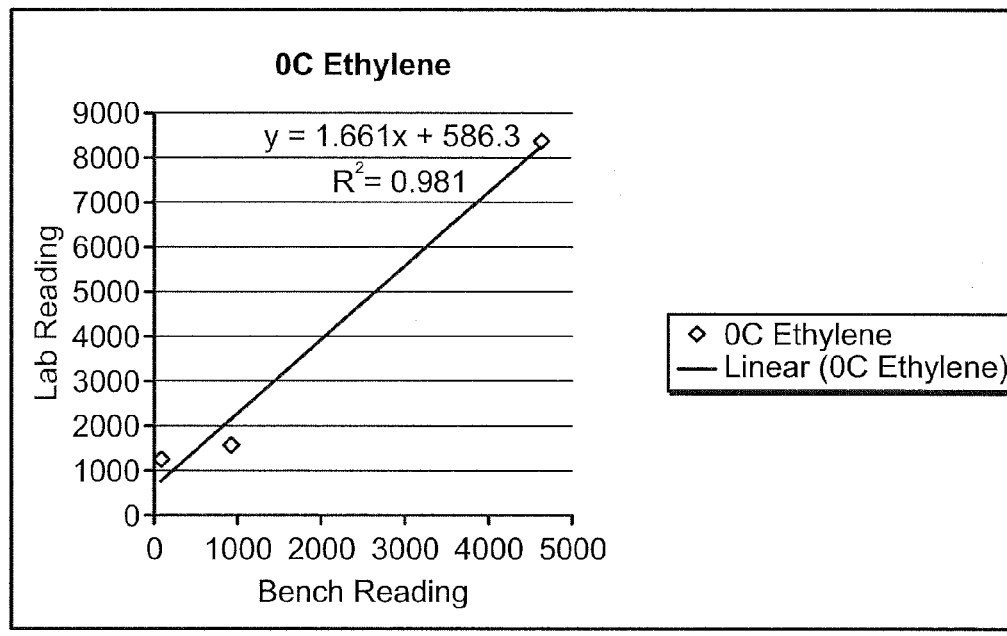
FIG. 25 shows test data in accordance with one or more embodiments.
Figure 26:
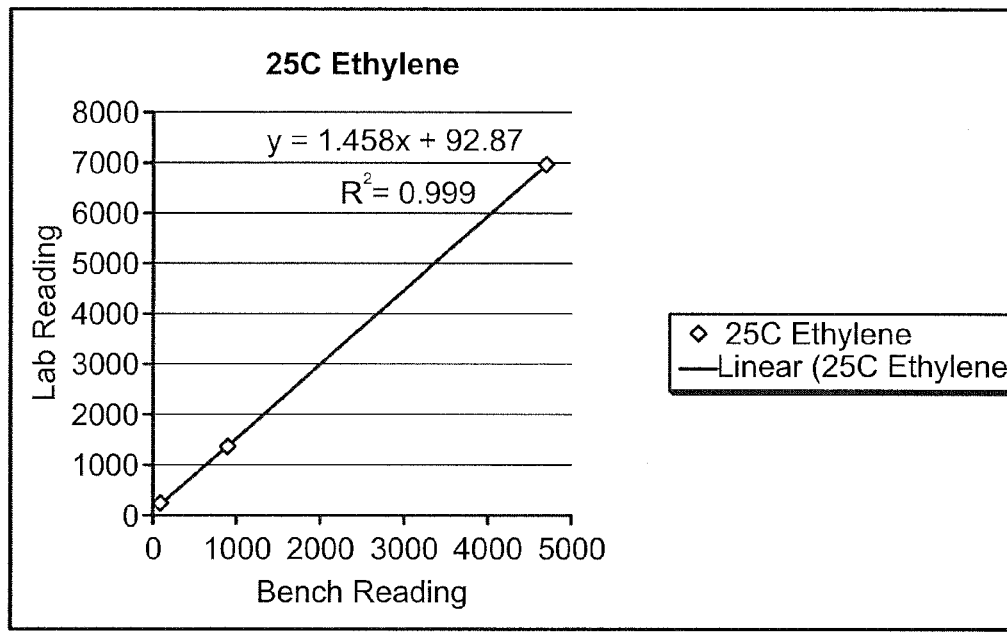
FIG. 26 shows test data in accordance with one or more embodiments.
Figure 27:
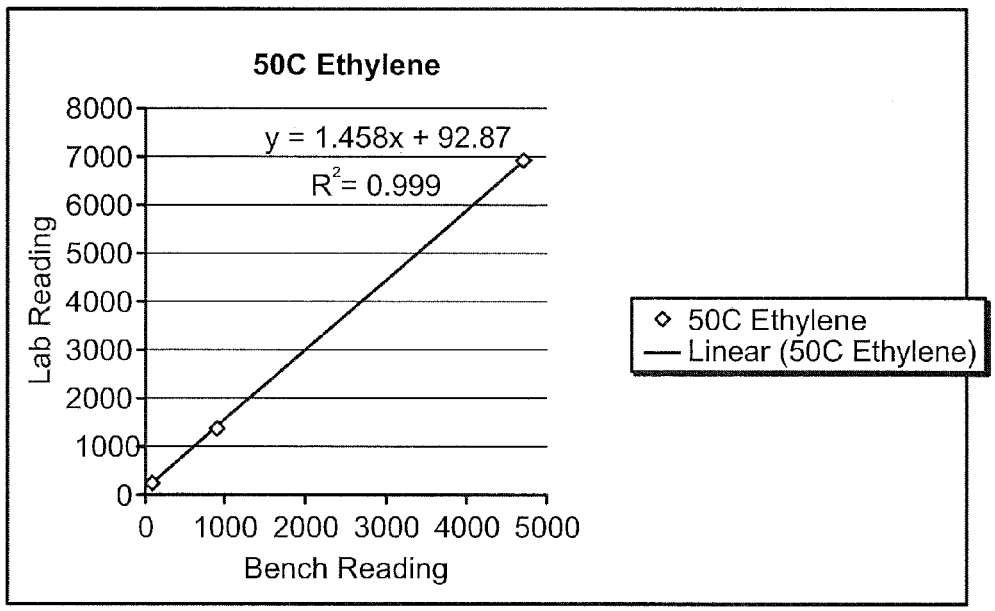
FIG. 27 shows test data in accordance with one or more embodiments.
Figure 28:
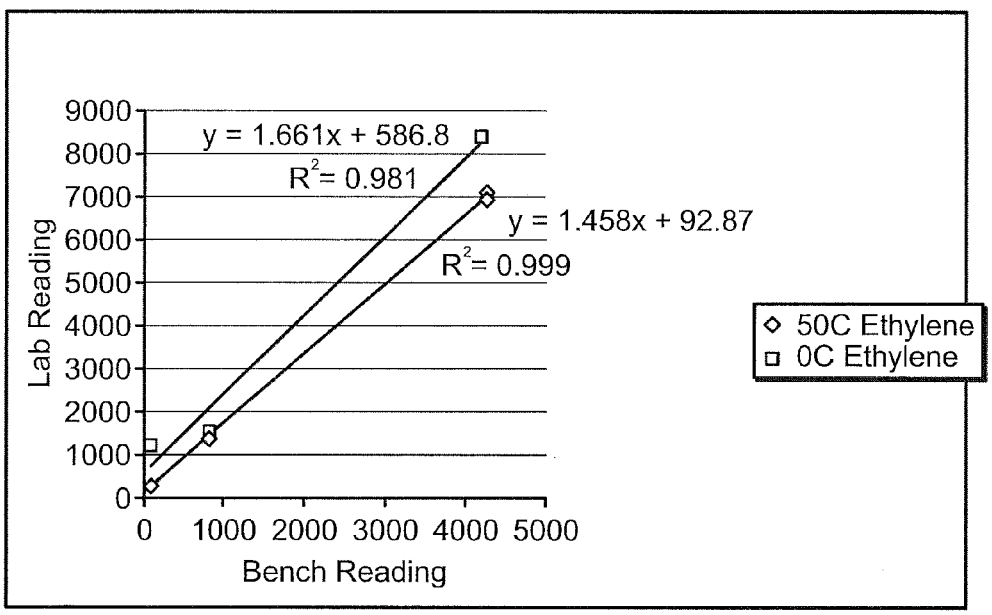
FIG. 28 shows test data in accordance with one or more embodiments.
Figure 29:
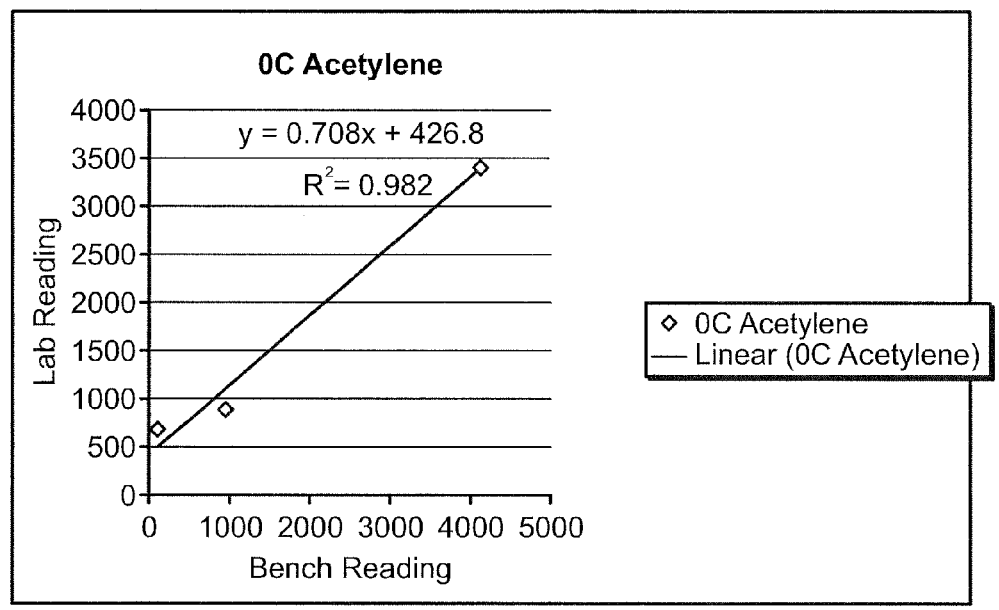
FIG. 29 shows test data in accordance with one or more embodiments.
Figure 30:
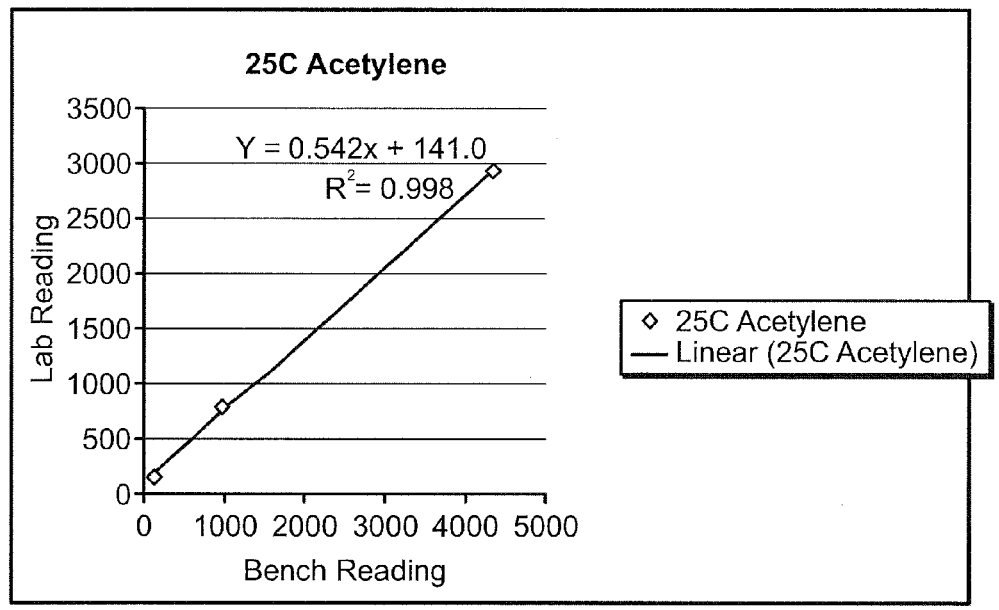
FIG. 30 shows test data in accordance with one or more embodiments.
Figure 31:
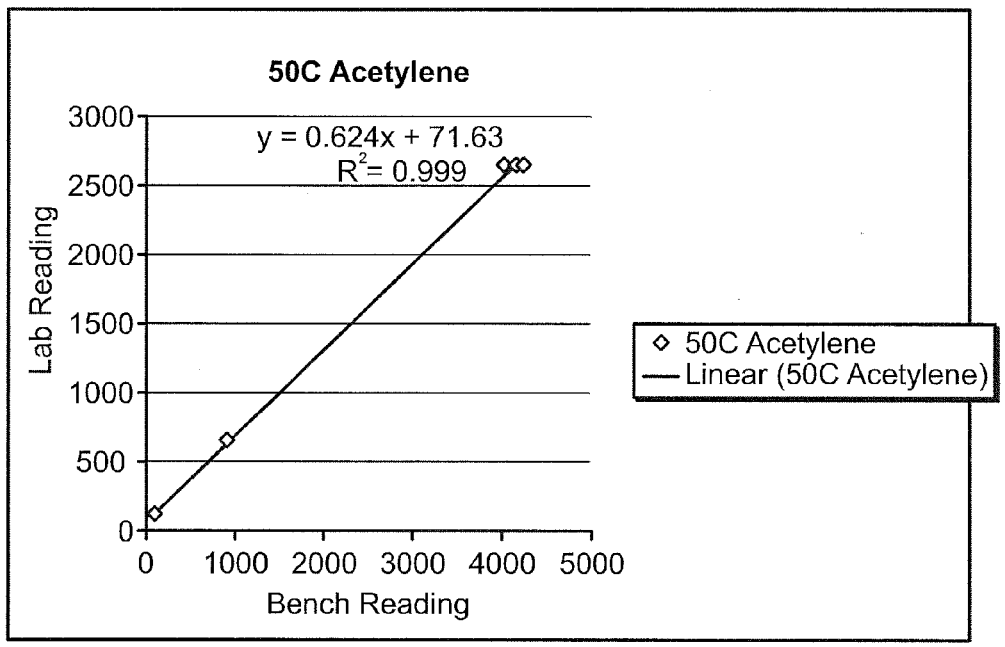
FIG. 31 shows test data in accordance with one or more embodiments.
Figure 32:
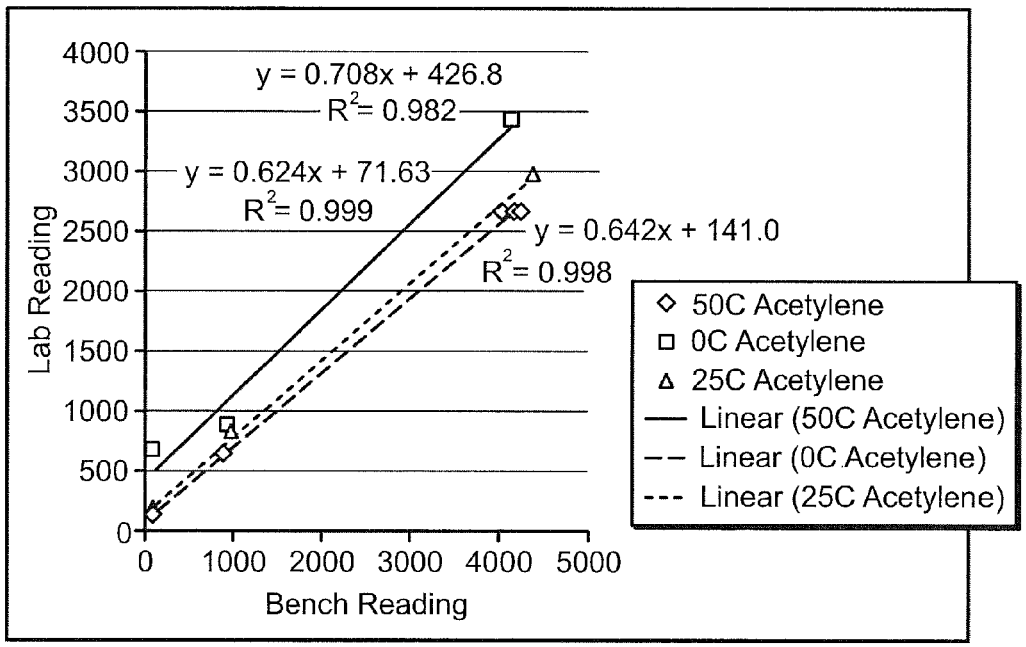
FIG. 32 shows test data in accordance with one or more embodiments.
Figure 33:
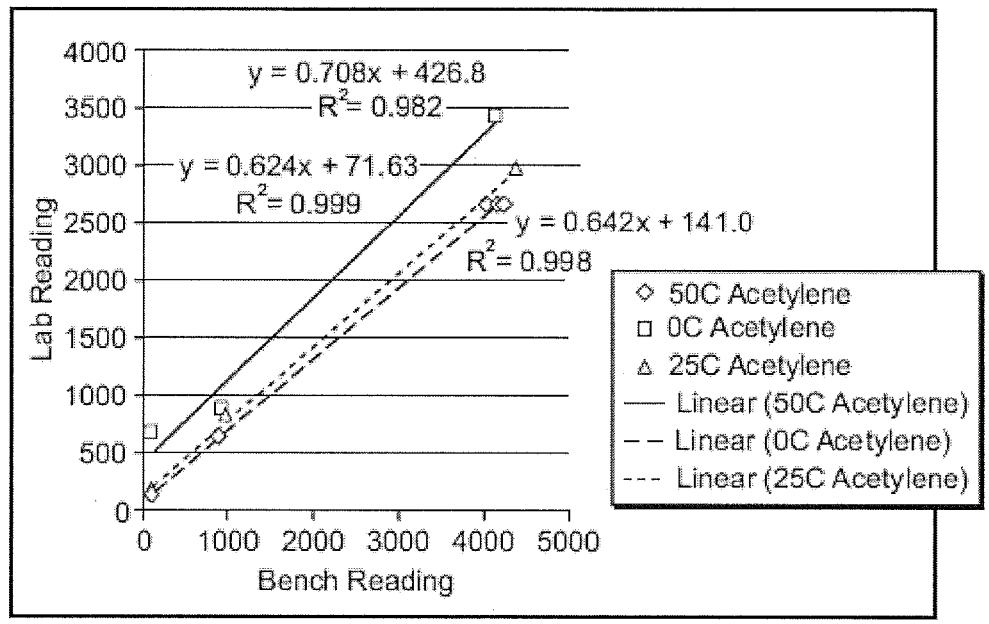
FIG. 33 shows test data in accordance with one or more embodiments.

FIG. 17 shows an example of the calibration curve of acetylene from 0 to 10,000 ppm showing a correlation between the present disclosure and headspace method.

FIG. 18 shows one example methodology that may be used in the instrument that may use the gas concentrations shown in FIGS. 7-10 and convert them into asset health and condition indicators. For example, in the case of rapid rise in ethylene and acetylene and ethylene/acetylene<1, the condition of the LTC is normal, thus triggering a "Normal" indicator, e.g., green light. No action is necessary other than to monitor the sample on a regular schedule appropriate under normal conditions, e.g., every six months. However, if a rapid rate of rise of acetylene above 1000 ppm is detected, a "Caution" indication is triggered, e.g., a yellow light. Such condition may be linked to mechanical activity in the LTC. Accordingly, the appropriate response may be to put the LTC on a watch list and sample every three months. Furthermore, if an ethylene rise of 1000 to 5000 ppm is detected, the ethylene rise is greater than the acetylene rise, and the ratio of ethylene/acetylene is greater than 1, a "Warning" indication is triggered, e.g., amber light. Such an indication might rise to the level that the problem is detectable by the eye and repairs should be immediately undertaken. This indication might be associated with an LTC that is approaching "critical condition." Accordingly, sample should be taken within one month and the LTC should be replaced within 1-2 weeks if confirmation is obtained by way of the lab analysis. Finally, an "Alarm" state, e.g., a red indicator may be triggered if a massive rate of rise of $C_2H_4$ accompanied by a ratio of ethylene/acetylene much greater than 1. Such a scenario likely indicates major damage to the LTC that would require a complete overhaul. Accordingly, the LTC may need to be taken offline within 1 day. One of ordinary skill will appreciate that many different methodologies may be deployed in accordance with one or more embodiments and that the above is laid out merely as one example. For example, the warning light colors may vary, the specific ratio of ethylene to acetylene at which different indicators are set, etc. may vary without departing from the scope of embodiments disclosed herein.

Advantageously the system for monitoring asset health by dissolved gas measurement in accordance with one or more embodiments disclosed herein may be a dedicated system to measure the asset health of a transformer or a LTC. For example, in the case of a dedicated a monitor module dedicated to a LTC, the module may be deployed using either a flow-through installation adaptor or signal valve installation adaptor as described above. Furthermore as a result of the ability to dedicate the module to the monitoring of an LTC, the software and hardware may be further adapted to compute various gas ratios on line, i.e., by way of a permanently installed on-line monitor module that is attached to the LTC, e.g., ethylene/acetylene without the need to take a sample and perform offsite lab tests. In addition, as a dedicated LTC instrument, the system may comply with the IEE standard for dissolved gas analysis in transformer load tap changers, or Std C57.139-2010.

Furthermore, in accordance with one or more embodiments, the system may allow for alarm conditions, such as those described above in reference to FIG. 18 for not only gas ratios, but also alarm limits may be set for gas quantity (e.g., in ppm), or rate of change of gas quantity.

FIGS. 19-32 show additional examples of test data for the instrument.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for analyzing gas dissolved within a fluid filled asset, the method comprising:
   extracting fluid from the fluid filled asset;
   isolating the extracted fluid from the fluid filled asset using one of a valve or a pump;
   circulating the extracted fluid through a first fluid loop;
   passing the extracted fluid along a first side of at least one gas permeable membrane;
   extracting gas from a second side of the at least one gas permeable membrane;
   circulating the extracted gas through a second fluid loop, wherein the first fluid loop and the second fluid loop are separated by the at least one gas permeable membrane;
   controlling a pressure differential across the at least one gas permeable membrane to a predetermined pressure differential;
   providing the extracted gas to a gas analysis unit disposed within the second fluid loop; and
   periodically determining a chemical makeup of the extracted gas using the gas analysis unit.

2. The method of claim 1 wherein controlling the pressure differential comprises:
   measuring a first pressure applied to the first side of the at least one gas permeable membrane;
   measuring a second pressure applied to the second side of the at least one gas permeable membrane, wherein the second side of the at least one gas permeable membrane is disposed within the second fluid loop; and
   controlling a fluid pump disposed in the first fluid loop to control the pressure differential based on the measured first and second pressures.

3. The method of claim 1, wherein controlling the pressure differential comprises:
   measuring a first pressure applied to the first side of the at least one gas permeable membrane, wherein the first side of the at least one gas permeable membrane is disposed within the first fluid loop;
   measuring a second pressure on the second side of the at least one gas permeable membrane, wherein the second side of the at least one gas permeable membrane is disposed within the second fluid loop;
   controlling a fluid pump disposed in the first fluid loop; and
   controlling a gas pump disposed in the second fluid loop;
   wherein controlling the gas pump and fluid pump controls the differential pressure based on the value of the first pressure and the second pressure.

4. The method of claim 1, wherein the pressure differential across the at least one membrane is maintained at approximately 0.5 psi.

5. The method of claim 1, further comprising extracting fluid from the fluid filled asset through a probe coupled to the valve, the valve disposed on the fluid filled asset, and returning the extracted fluid to the valve.

6. The method of claim 5, wherein the probe is configured in a dual passage geometry comprising a fluid inlet passage through which fluid from the asset is extracted and a fluid outlet passage through which fluid is returned to the asset.

7. The method of claim 1, further comprising extracting the fluid from the fluid filled asset through an inlet valve disposed on a preexisting filtration unit of the fluid filled asset and returning the fluid to an outlet valve disposed on the preexisting filtration unit.

8. The method of claim 1, further comprising extracting fluid from the fluid filled asset through the valve, the valve disposed on the fluid filled asset, and returning the fluid to the fluid filled asset through a second valve, the second valve disposed on the fluid filled asset.

9. The method of claim 1, further comprising periodically calibrating the gas analysis unit by purging at least a portion of the second fluid loop with a purge gas.

10. The method of claim 1, further comprising controlling a temperature of the fluid circulating in the first fluid loop.

11. The method of claim 10, wherein the controlling the temperature of the fluid circulating in the first fluid loop comprises circulating the fluid through a heated reservoir.

12. The method of claim 1, wherein determining the chemical makeup of the extracted gas includes detecting at least one gas selected from a group consisting of $C_2H_4$, $C_2H_2$, $H_2$, CO, $H_2O$, $CO_2$, $CH_4$, $C_2H_6$, $O_2$, and $N_2$.

13. The method of claim 1, wherein the fluid filled asset is one selected from a group consisting of a dielectric oil filled transformer and a dielectric oil filled load tap changer.

14. The method of claim 1, wherein the fluid is dielectric oil.

15. The method of claim 1, wherein the gas permeable membrane is a polymer membrane that is permeable to gas and impermeable to liquid.

16. The method of claim 9 wherein the purge gas is air.

17. A system for analyzing dissolved gas in a fluid. filled asset comprising:
   a fluid extraction unit configured to extract fluid from the fluid filled asset;
   an isolation device coupled to the fluid filled asset and configured to isolate the extracted fluid from the fluid filled asset;
   a fluid pump configured to circulate the fluid though a first fluid loop;
   a gas extraction unit in the first fluid loop configured to extract dissolved gas from the circulating fluid, the gas extraction unit comprising at least one gas permeable membrane;

a gas pump configured to circulate the extracted gas through a second fluid loop, wherein the first fluid loop and the second fluid loop are separated by the at least one gas permeable membrane;

a pressure control unit configured to control a differential pressure across the at least one gas permeable membrane to a predetermined pressure differential; and a gas analysis unit in the second fluid loop, configured to receive the extracted gas, wherein the gas analysis unit is further configured to periodically determine, at specific intervals, the chemical makeup of the extracted gas.

18. The system of claim 17, wherein the pressure control unit controls the pressure differential across the at least one gas permeable membrane by controlling the fluid pressure in the first fluid loop.

19. The system of claim 17 further comprising:

a first pressure sensor mounted in the first fluid loop and configured to measure a first pressure applied to a first side of the at least one gas permeable membrane wherein the first side of the at least one gas permeable membrane is disposed within the first fluid loop; and a second pressure sensor mounted in the second fluid loop and configured to measure a second pressure applied to a second side of the at least one gas permeable membrane wherein the second side of the at least one gas permeable membrane is disposed within the second fluid loop, wherein the pressure control unit controls a fluid pump disposed in the first fluid loop to control the differential pressure based on the measured first and second pressures.

20. A method for analyzing gas dissolved within a fluid filled asset, the method comprising:

circulating fluid from the fluid filled asset through an extraction loop;

circulating a portion of the fluid in the extraction loop through a first fluid loop;

passing the portion of the fluid in the first fluid loop along a first side of at least one gas permeable membrane, the gas permeable membrane being pressure isolated from the fluid filled asset with one of a valve or a puma during both circulating steps;

extracting gas from a second side of the at least, one gas permeable membrane;

circulating the extracted gas through a second fluid mop, wherein the first fluid loop and the second fluid loop are separated by the at least one gas permeable membrane;

controlling a pressure differential across the at least one gas permeable membrane to a predetermined pressure differential;

providing the extracted gas to a gas analysis unit disposed within the second fluid loop; and periodically determining a chemical makeup of the extracted gas using the gas analysis unit.

* * * * *